(12) United States Patent
Lin et al.

(10) Patent No.: US 12,106,497 B2
(45) Date of Patent: Oct. 1, 2024

(54) METHOD AND NAVIGATION SYSTEM FOR REGISTERING TWO-DIMENSIONAL IMAGE DATA SET WITH THREE-DIMENSIONAL IMAGE DATA SET OF BODY OF INTEREST

(71) Applicant: Remex Medical Corp., Taichung (TW)

(72) Inventors: Sheng-Fang Lin, Taiwan (TW); Ying-Yi Cheng, Taiwan (TW); Chen-Tai Lin, Taiwan (TW); Shan-Chien Cheng, Taiwan (TW)

(73) Assignee: REMEX MEDICAL CORP., Taichung (TW)

( * ) Notice: Subject to any disclaimer, the term of this patent is extended or adjusted under 35 U.S.C. 154(b) by 111 days.

(21) Appl. No.: 17/856,289

(22) Filed: Jul. 1, 2022

(65) Prior Publication Data

US 2023/0154019 A1 May 18, 2023

Related U.S. Application Data

(60) Provisional application No. 63/264,250, filed on Nov. 18, 2021.

(51) Int. Cl.
*G06T 7/30* (2017.01)
*A61B 34/10* (2016.01)
(Continued)

(52) U.S. Cl.
CPC .............. *G06T 7/344* (2017.01); *A61B 34/10* (2016.02); *A61B 34/20* (2016.02); *A61B 90/36* (2016.02);
(Continued)

(58) Field of Classification Search
CPC .. G06T 7/344; G06T 7/80; G06T 7/50; G06T 7/30; G06T 7/33; G06T 7/337;
(Continued)

(56) References Cited

U.S. PATENT DOCUMENTS 6,470,207 B1 10/2002 Simon et al.
10,194,131 B2 * 1/2019 Casas .................. H04N 13/111
(Continued)

OTHER PUBLICATIONS

Wein, Wolfgang, "Intensity based rigid 2D-3D registration algorithms for radiation therapy", Dec. 15, 2003, Retrieved from the internet onFeb. 8, 2023: URL: https://campar.in.tum.de/twiki/pub/Main/WolfgangWein/thesis.pdf.
(Continued)

*Primary Examiner* — Wesner Sajous
(74) *Attorney, Agent, or Firm* — Merchant & Gould P.C.

(57) ABSTRACT

A method for registering a two-dimensional image data set with a three-dimensional image data set of a body of interest is discloses herein. The method includes the following steps: adjusting a first virtual camera according to a distance parameter calculated corresponding to the two-dimensional image data set and the body of interest; rotating the first virtual camera according to an angle difference between a first vector and a second vector; and rotating the first virtual camera according to an angle which is corresponding to a maximum similarity value of a plurality of similarity values calculated in accordance with reconstructed images of the three-dimensional image data set which includes one generated by the first virtual camera and the others generated by other virtual cameras with different angles or different pixels from the one generated by the first virtual camera and the two-dimensional image data set.

20 Claims, 14 Drawing Sheets

2000

Adjusting a first virtual camera according to a distance parameter calculated corresponding to the two-dimensional image data set and the body of interest — 2100

Rotating the first virtual camera according to an angle difference between a first vector and a second vector — 2200

Rotating the first virtual camera according to an angle which is corresponding to a maximum similarity value of a plurality of similarity values calculated in accordance with reconstructed images of the three-dimensional image data set which includes one generated by the first virtual camera and the others generated by other virtual cameras with different angles or different pixels from the one generated by the first virtual camera and the two-dimensional image data set — 2300

(51) Int. Cl.

| | | |
|---|---|---|
| *A61B 34/20* | (2016.01) | |
| *A61B 90/00* | (2016.01) | |
| *G06T 7/00* | (2017.01) | |
| *G06T 7/33* | (2017.01) | |
| *G06T 7/50* | (2017.01) | |
| *G06T 7/70* | (2017.01) | |
| *G06T 7/80* | (2017.01) | |
| *G06T 11/00* | (2006.01) | |
| *G06T 15/20* | (2011.01) | |
| *G06T 19/20* | (2011.01) | |

(52) U.S. Cl.
CPC ............. *G06T 7/0014* (2013.01); *G06T 7/30* (2017.01); *G06T 7/33* (2017.01); *G06T 7/337* (2017.01); *G06T 7/50* (2017.01); *G06T 7/70* (2017.01); *G06T 7/80* (2017.01); *G06T 11/005* (2013.01); *G06T 11/008* (2013.01); *G06T 15/20* (2013.01); *G06T 19/20* (2013.01); *A61B 2034/2057* (2016.02); *A61B 2090/367* (2016.02); *G06T 2200/04* (2013.01); *G06T 2207/10072* (2013.01); *G06T 2207/10081* (2013.01); *G06T 2207/10088* (2013.01); *G06T 2207/10101* (2013.01); *G06T 2207/10121* (2013.01); *G06T 2207/10136* (2013.01); *G06T 2207/30004* (2013.01); *G06T 2207/30012* (2013.01); *G06T 2207/30204* (2013.01); *G06T 2210/41* (2013.01); *G06T 2219/2004* (2013.01)

(58) Field of Classification Search
CPC ....... G06T 7/70; G06T 7/0014; G06T 11/30; G06T 11/008; G06T 15/20; G06T 19/20; G06T 2207/10072; G06T 2207/10081; G06T 2207/10088; G06T 10/101; G06T 10/121; G06T 10/10136; G06T 10/30004; G06T 2207/30012; G06T 2207/30204; G06T 2200/04; G06T 2210/41; G06T 2219/2004; A61B 2090/367; A61B 2034/2057; A61B 34/10; A61B 34/20; A61B 90/36
USPC ........................................................ 345/419
See application file for complete search history.

(56) References Cited

U.S. PATENT DOCUMENTS

| | | | |
|---|---|---|---|
| 2015/0117605 | A1 | 4/2015 | Sugiura et al. |
| 2019/0149797 | A1* | 5/2019 | Casas .................. H04N 13/156 348/47 |
| 2019/0349559 | A1* | 11/2019 | Casas ..................... A61B 34/20 |
| 2020/0138518 | A1* | 5/2020 | Lang ...................... A61B 90/37 |
| 2020/0221060 | A1* | 7/2020 | Casas .................. H04N 13/111 |
| 2020/0405359 | A1* | 12/2020 | Hayes ................. A61B 17/7079 |
| 2021/0037224 | A1* | 2/2021 | Casas ..................... A61B 34/10 |
| 2021/0160472 | A1* | 5/2021 | Casas ..................... G06F 3/017 |
| 2021/0192759 | A1* | 6/2021 | Lang ...................... A61B 34/20 |
| 2022/0079675 | A1* | 3/2022 | Lang ...................... G02B 30/52 |
| 2023/0149083 | A1* | 5/2023 | Lin .......................... G06T 7/33 606/130 |
| 2023/0154018 | A1* | 5/2023 | Lin .......................... G06T 7/50 382/131 |
| 2023/0154021 | A1* | 5/2023 | Lin ......................... G06T 7/337 382/131 |

OTHER PUBLICATIONS

Russakoff, D.B., et al., "Fast generation of digitally reconstructed radiographs using attenuation fields with application to 2D-3D image registration", IEEE Transactions on Medical Imaging, IEEE, USA, vol. 24, No., 11, Nov. 1, 2005.

* cited by examiner

METHOD AND NAVIGATION SYSTEM FOR REGISTERING TWO-DIMENSIONAL IMAGE DATA SET WITH THREE-DIMENSIONAL IMAGE DATA SET OF BODY OF INTEREST

RELATED APPLICATIONS

This application claims priority to U.S. Provisional Application Ser. No. 63/264250, filed Nov. 18, 2021, the entire contents of which are incorporated herein by reference as if fully set forth below in its entirety and for all applicable purposes.

BACKGROUND

Field of Invention

The present disclosure relates to a method and a navigation system for establishing a relation between a two-dimensional image data and three-dimensional image data both corresponding to a body of interest. More particularly, the present disclosure relates to a method and a navigation system for registering a two-dimensional image data set with a three-dimensional image data set of a body of interest.

Description of Related Art

At present, the rate of occurrence of diseases corresponding to the spine is increasing day by day, and the health of human is seriously affected. Spinal surgery is a main treatment for spinal diseases, and how to minimize wounds during and after a procedure becomes more and more important, such that infection risks can be reduced and patients are able to quickly recover without hospitalization. For this purpose, an image guided surgical procedure with a navigation system is introduced into spinal surgeries. During the image guided medical procedure, the area of interest of a patient that has been imaged is displayed on a display of the navigation system. Meanwhile, the system can track surgical instruments and/or implants and then integrate their simulated images with the area of interest of the patient body. By taking advantage of such a procedure and system, physicians are able to see the location of the instruments and/or implants relative to a target anatomical structure without the need to frequent use of C-Arm fluoroscopy throughout the entire surgical procedure is generally disclosed in U.S. Pat. No. 6,470,207, entitled "Navigational Guidance Via Computer-Assisted Fluoroscopic Imaging," issued Oct. 22, 2002, which is incorporated herein by reference in its entirety.

However, the spine navigation system usually needs to use the X-ray inspection for obtaining the internal body of the patient. The patient is therefore in danger due to the radiation exposure. In view of the foregoing, problems and disadvantages are associated with existing systems that require further improvement. However, those skilled in the art have yet to find a solution.

There are many ways to achieve two-directional (2D) to three-directional (3D) registration by adopting obtained 2D images to register 3D images which are known in the art. The registrations from 2D to 3D include contour algorithms, point registration algorithms, surface registration algorithms, density comparison algorithms, and pattern intensity registration algorithms. The foregoing registrations, however, need a great deal of calculation and therefore, usually take several minutes to execute the 2D to 3D registration. Actually, some of these registrations may take upwards of twenty minutes to an hour to execute the registration. Furthermore, these registration processes could also result in an inexact registration after waiting for such long time.

In view of the foregoing, problems and disadvantages are associated with existing technologies, that require further improvement, and there is a need to provide a method and equipment for executing 2D to 3D registration in a more accurate and efficient way. Moreover, the flows of the method for executing 2D to 3D registration shall also be improved.

In addition, 2D images (e.g., X-ray images) generally cover more than one level of vertebrae. Matching 2D images with digitally reconstructed radiographs (DRR) from computed tomography (CT) data is not efficient and easy to cause registration failures, errors, or inaccuracy due to interference in regions of interest such as pedicle screw, cage, ribs, and Ilium. Specialized algorithm focusing on separated local comparison instead of global matching may be used to help the comparison in such anatomical images. Even if a 2D to 3D registration is performed, there are still problems and disadvantages, for example, more time consumption and less accuracy. Therefore, how to make the 2D to 3D registration become faster and more accurate is a purpose for the industry. In particular, considering separated local comparison is introduced into 2D to 3D registration, developing a pre-process capable to further shorten the registration period and improve the accuracy is in demand.

SUMMARY

The foregoing presents a simplified summary of the disclosure in order to provide a basic understanding to the reader. This summary is not an extensive overview of the disclosure and it does not identify key/critical elements of the present disclosure or delineate the scope of the present disclosure. Its sole purpose is to present some concepts disclosed herein in a simplified form as a prelude to the more detailed description that is presented later.

One aspect of the present disclosure is to provide a method for registering a two-dimensional image data set with a three-dimensional image data set of a body of interest. The method comprises following steps: adjusting a first virtual camera according to a distance parameter calculated corresponding to the two-dimensional image data set and the body of interest: rotating the first virtual camera according to an angle difference between a first vector and a second vector, wherein the first vector is calculated from two spatial marks in the three-dimensional image data set, and the second vector is calculated from two first plain marks in the two-dimensional image data set; and rotating the first virtual camera according to an angle which is corresponding to a maximum similarity value of a plurality of similarity values calculated in accordance with reconstructed images of the three-dimensional image data set which includes one generated by the first virtual camera and the others generated by other virtual cameras with different angles or different pixels from the one generated by the first virtual camera and the two-dimensional image data set for implementing in the two-dimensional image data set to the three-dimensional image data set registration of a navigation system after adjusting and rotating.

Another aspect of the present disclosure is to provide a navigation system for registering a two-dimensional image data set with a three-dimensional image data set of a body of interest. The navigation system comprises a memory and a processor. The memory is configured to store a plurality of commands. The processor is configured to obtain the plurality of commands from the memory to perform following steps: adjusting a first virtual camera according to a distance parameter calculated corresponding to the two-dimensional image data set and the body of interest; rotating the first virtual camera according to an angle difference between a first vector and a second vector, wherein the first vector is calculated from two spatial marks in the three-dimensional image data set, and the second vector is calculated from two first plain marks in the two-dimensional image data set; and rotating the first virtual camera according to an angle which is corresponding to a maximum similarity value of a plurality of similarity values calculated in accordance with reconstructed images of the three-dimensional image data set which includes one generated by the first virtual camera and the others generated by other virtual cameras with different angles or different pixels from the one generated by the first virtual camera and the two-dimensional image data set for implementing in the two-dimensional image data set to the three-dimensional image data set registration of the navigation system after adjusting and rotating.

In view of the foregoing, the method and the navigation system of the present disclosure may provide an initialization alignment before a typical 2D to 3D registration process. Since an additional alignment such as the initialization alignment is performed in advance, the overall 2D to 3D registration becomes faster and more accurate. It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

According to the usual mode of operation, various features and elements in the figures have not been drawn to scale, which are drawn to the best way to present specific features and elements related to the disclosure. In addition, among the different figures, the same or similar element symbols refer to similar elements/components.

DESCRIPTION OF THE EMBODIMENTS

To make the contents of the present disclosure more thorough and complete, the following illustrative description is given with regard to the implementation aspects and embodiments of the present disclosure, which is not intended to limit the scope of the present disclosure. The features of the embodiments and the steps of the method and their sequences that constitute and implement the embodiments are described. However, other embodiments may be used to achieve the same or equivalent functions and step sequences.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Figure 1:
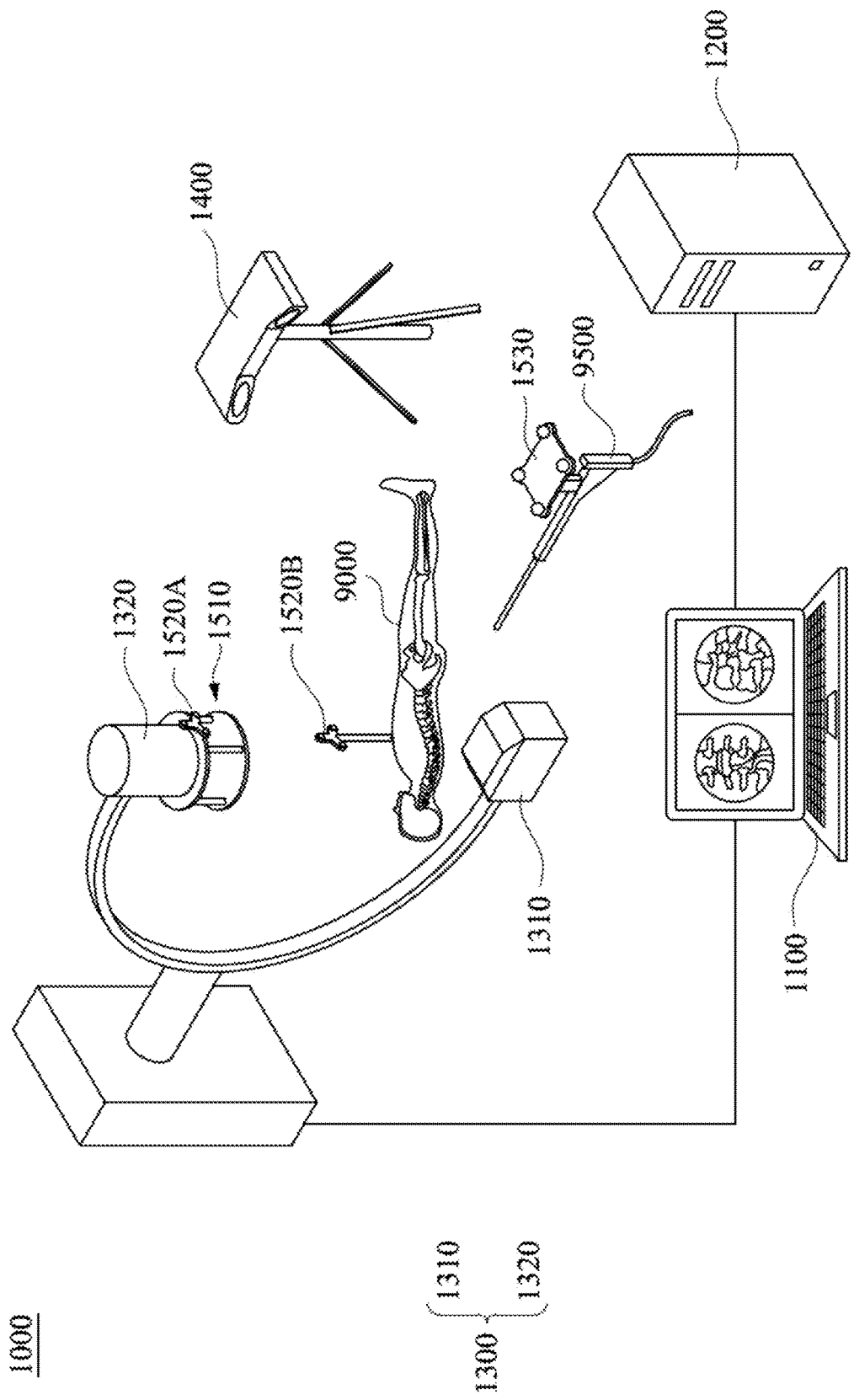
FIG. 1 depicts a schematic diagram of a navigation system according to one embodiment of the present disclosure.

FIG. 1 depicts a schematic diagram of a navigation system 1000 having a calculating device 1100, a database 1200, and an optical tracker 1400 according to one embodiment of the present disclosure. The navigation system 1000 can be used to navigate an instrument 9500 during a surgical operation of an object 9000, but the present disclosure is not limited thereto. In some embodiments, the navigation system 1000 can be used to navigate any kind of tools during any type of operations depending on actual requirements. For instances, the navigation system 1000 can be used to navigate screws, graspers, clamps, surgical scissors, cutters, needle drivers, retractors, distracters, dilators, suction tips and tubes, sealing devices, irrigation and injection needles, powered devices, scopes and probes, carriers and appliers, ultrasound tissue disruptors, cryotomes and cutting laser guides, and measurement devices. The navigation system 1000 can also be used to navigate any type of implant including orthopedic implants, spinal implants, cardiovascular implants, neurovascular implants, soft tissue implants, or any other devices implanted in an objective 9000 such as a patient.

The calculating device 1100 can be but not limited to a computer, a desktop, a notebook, a tablet, or any other devices that can perform calculating function. The database 1200 can be but not limited to a data storage, a computer, a server, a cloud storage, or any other devices that can store data. The database 1200 is used to store, pre-acquired three-dimensional (3D) image data set of the object 9000. The 3D image data set can be obtained by using a computerized tomography (CT) to scan the object 9000.

The imaging device 1300 can be established and performed separately from the navigation system 1000, and the imaging device 1300 can be but not limited to a C-arm mobile fluoroscopy machine or a mobile X-ray image intensifier. The imaging device 1300 includes a X-ray emitter 1310 and a X-ray receiver 1320. The former emits X-rays that penetrate the body of the object 9000, and the latter receives and converts the X-rays into digital two-dimensional (2D) images on a display of imaging device 1300. According to the planes along which the imaging device 1300 obtains images, the 2D images may be an anterior/posterior (AP) image and a lateral view (LA) 2D image of the object 9000. The object 9000 can be but not limited to a patient.

The calibrator 1510 including calibration markers is used to both calibrate the imaging device 1300 and track the location of the imaging device 1300 during an image is obtained. The calibrator 1510 is included in or disposed on the X-ray receiver 1320, and the dynamic reference frames 1520A are disposed on or close to the X-ray receiver 1320 and the body of interest of the object 9000. The calibrator 1510 is in the path from the X-ray emitter 1310 to the X-ray receiver 1320 and opaque-or semi-opaque to the X-ray. Therefore, the X-ray entering the object 9000 and also the calibrator 1510 are partially absorbed by particular tissues and the calibration markers in the calibrator 1510 before received by the X-ray receiver 1320 in operation. This makes the two-dimensional images present the body of interest of the object 9000 and the calibration markers of the calibrator 1510. The calculating device 1100 may acquire the relation of the X-ray emitter 1310 and the X-ray receiver 1320 by calculating the pattern of the calibration markers presented on the two-dimensional images. The AP two-dimensional image and the LA two-dimensional image of the vertebral bodies of interest of the object 9000 are involved the two-dimensional image data set in the present embodiment. Alternatively, in another embodiment, it can be only AP two-dimensional image or LA two-dimensional image in the two-dimensional image data set. Then, the two-dimensional image data set can be transmitted as an electronic file to the calculating device 1100 for later use.

The three-dimensional image data set in the database 1200, the two-dimensional image data set generated from the imaging device 1300, the optical tracker 1400, the calibrators 1510, the dynamic reference frame 1520A, and the object 9000 have their own coordinates in different coordinate systems. The navigation system 1000 of the present disclosure can establish relations among those coordinate systems, such that surgeons may use the navigation system 1000 to navigate the instrument 9500 or during the surgical operation. The relation among those coordinates is described below. The calibrator 1510 and the dynamic reference frame 1520A are disposed on the X-ray receiver 1320, the location of the three can be substantially treated as the same, and therefore, the relation between the calibrator coordinate system and the imaging device coordinate system is established. The optical tracker 1400 then tracks the dynamic reference frame 1520A including reflector to introduce the calibrator 1510, the dynamic reference frame 1520A, and the X-ray receiver 1320 into the tracker coordinate system, and therefore, the location of the X-ray receiver 1320 in the tracker coordinate system is obtained. In some embodiments, the optical tracker 1400 can o track the calibrator 1530 including reflector to introduce the calibrator 1530 into the tracker coordinate system, and therefore, the location of the calibrator 1530 in the tracker coordinate system is obtained. Since the relation of the X-ray emitter 1310 and the X-ray receiver 1320 is acquired as described above, the location of the X-ray emitter 1310 in the tracker coordinate system can be acquired as well. It is noted that, the present disclosure is not limited to the structures and the operations as shown in FIG. 1, and it is merely an example for illustrating one of the implements of the present disclosure.

It is noted that the registration procedure of the navigation system 1000 substantially consists of three stages which are initialization alignment, 2D to 3D registration, and realignment. In some embodiments, the program installed in the navigation system 1000 runs through these three stages, further discussed herein. Alternatively, in other embodiments, the program can run only the initial alignment process, the 2D to 3D registration, the re-registration, or a combination thereof depending on the situations and/or the functions needed. More details will be discussed below.

Initialization Alignment

Before using the navigation system 1000, an initial alignment process would be performed to the navigation system 1000 so as to improve the efficiency and enhance the precision of the navigation system 1000, which will be described below.

Figure 2:
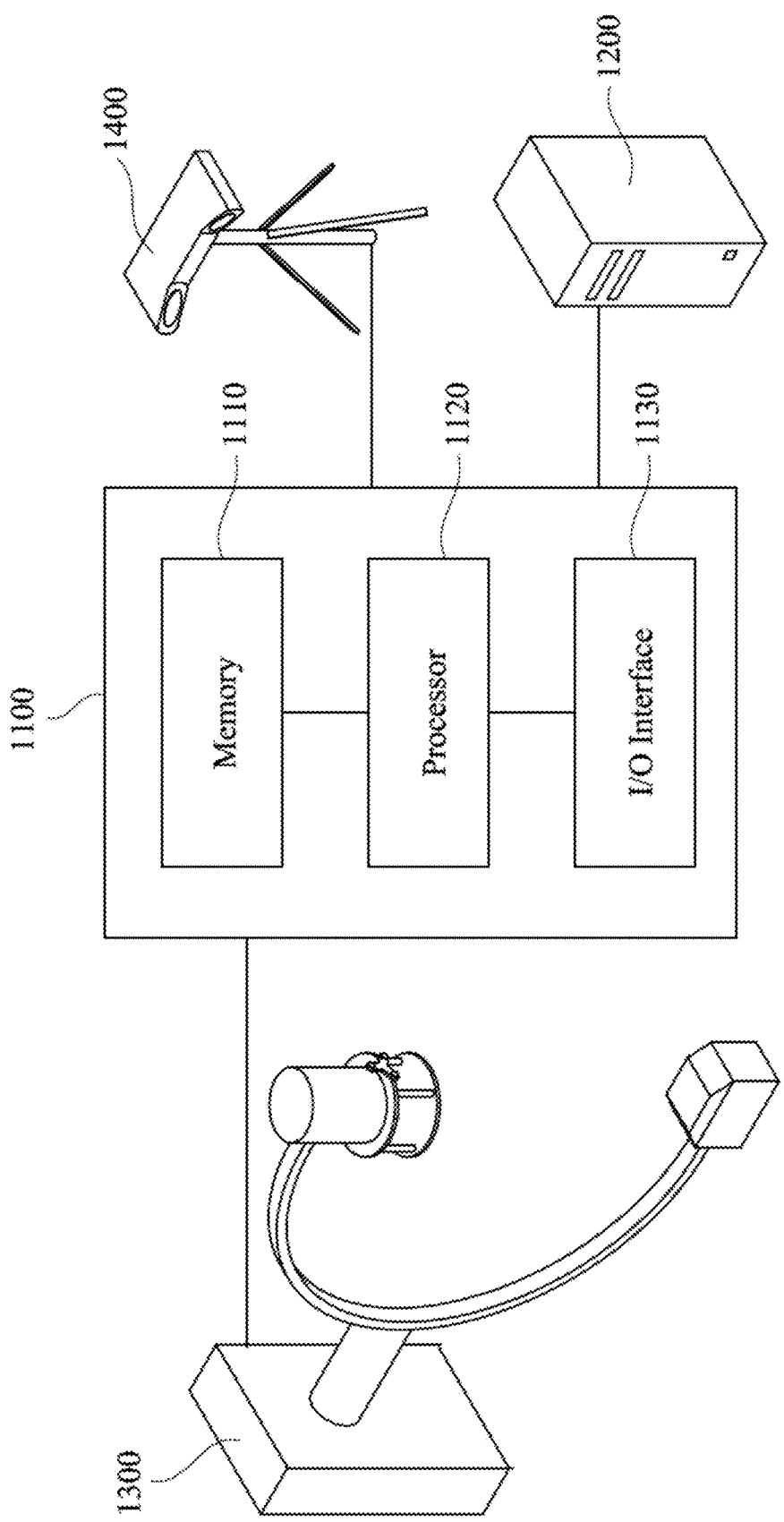
FIG. 2 depicts a schematic diagram of a calculating device, a database, and an optical tracker of the navigation system shown in FIG. 1 according to one embodiment of the present disclosure.

FIG. 2 depicts a schematic diagram of the calculating device 1100, the database 1200, and the optical tracker 1400 of the navigation system 1000 shown in FIG. 1 according to one embodiment of the present disclosure. As shown in the figure, the calculating device 1100 is electrically connected to the database 1200 and the imaging device 1300.

The calculating device 1100 includes a memory 1110, a processor 1120, and an I/O interface 1130. The processor 1120 is electrically connected to the memory 1110 and the I/O interface 1130. The memory 1110 is used to store a plurality of commands, and the processor 1120 is used to obtain the plurality of commands from the memory 1110 to perform steps of a method 2000 shown in FIG. 3 for registering a two-dimensional image data set with a three-dimensional image data set of a body of interest.

In some embodiments, the memory 1110 can include, but not limited to, at least one of a flash memory, a hard disk drive (HDD), a solid-state drive (SSD), a dynamic random access memory (DRAM) and a static random access memory or a combination thereof. In some embodiments, as being a non-transitory computer readable medium, the memory 1110 can store, the computer readable commands that can be accessed by the processor 1120.

In some embodiments, the processor 1120 can include, but not limited to, a single processor or an integration of multiple microprocessors, such as a central processing unit (CPU), a graphics processing unit (GPU) or an application-specific integrated circuit (ASIC), etc.

Figure 3:
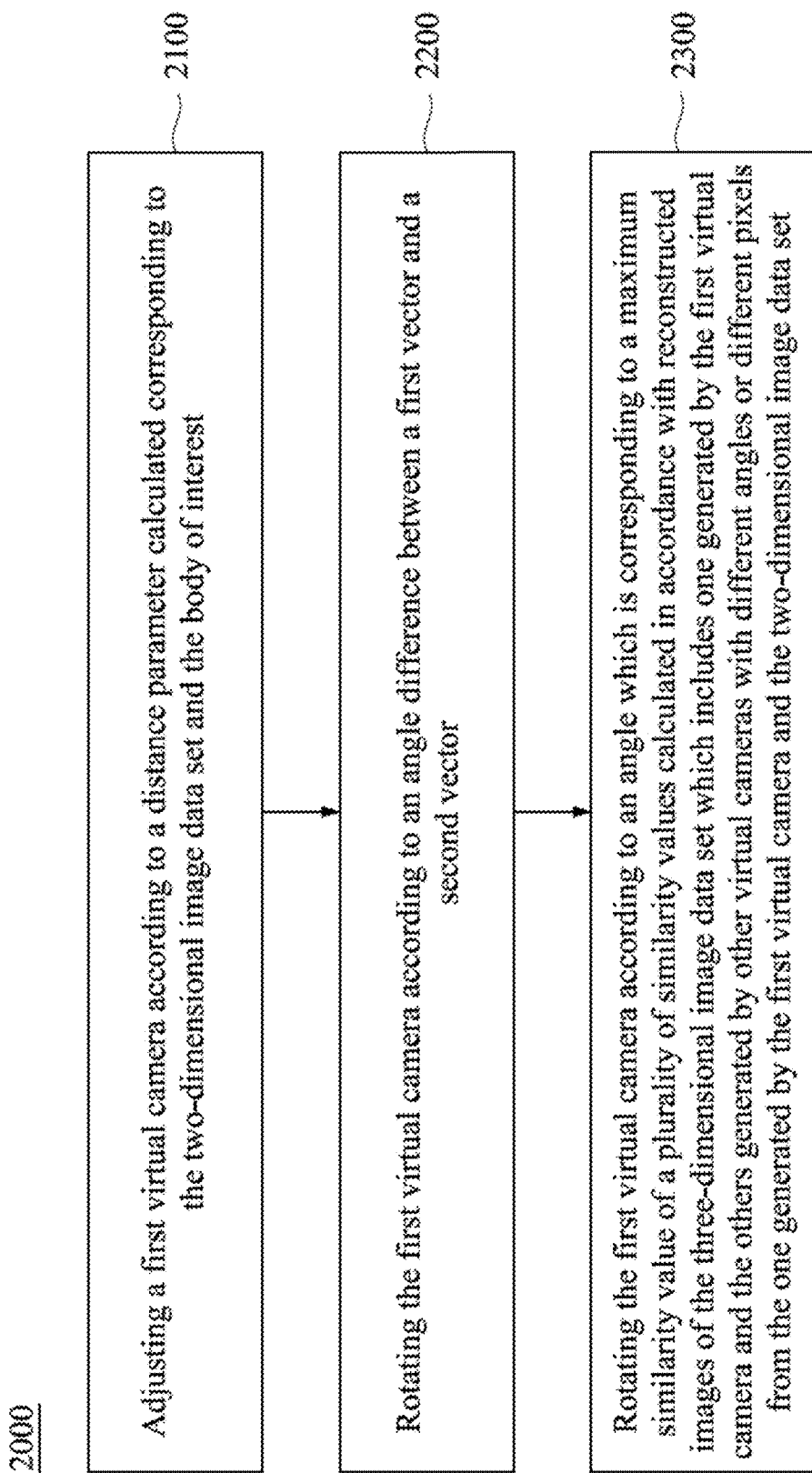
FIG. 3 depicts a flow diagram of a method for registering a two-dimensional image data set with a three-dimensional image data set of a body of interest according to one embodiment of the present disclosure.

Reference is now made to both FIG. 2 and FIG. 3. In operation, the step 2100 is performed by the processor 1120 to adjust a first virtual camera according to a distance parameter calculated corresponding to the two-dimensional image data set and the body of interest.

For example, the processor 1120 of the calculating device 1100 may obtain the X-ray images directly from the imaging device 1300 or pre-stored in the database 1200. As discussed above, the two-dimensional data set includes at least the AP and LA two-dimensional images which both include the calibrator 1510 in FIG. 1. The calibrator 1510 can be used to identify the location of the imaging device 1300 in operation in accordance with the abovementioned calculation of the relation. Once the location of the imaging device 1300 is acquired, the processor 1120 may estimate the distance between the X-ray emitter 1310 and the targeted vertebral body of interest in the objective 9000. The estimated distance then is converted to a distance parameter for by the processor 1120 of the calculating device 1100.

The initialization alignment 2000 according to the embodiment disclosed herein is illustrated. Briefly, the initialization alignment 2000 can include three steps 2100, 2200, 2300.

As a first step, the surgeon is asked to acquire a first image or an anterior/posterior (AP) image and a second image or a lateral (LA) image from the imaging device 1300. These images are used for refinement and navigation, but also to initialize the orientation. Since the imaging device 1300 includes the calibrator 1510 the location of the X-ray emitter 1310 during image acquisition with respect to the patient coordinate system is known (i.e., patient AP direction and patient LA direction). This knowledge is combined with the knowledge of how the patient 9000 is oriented during the three-dimensional volume scan by the setting of the user. Given the estimated orientation, digitally reconstructed radiographs (DRRs) are created from the three-dimensional data set acquired by CT scan. Owing to the DRRs being a kind of digital images, it is helpful to explain how and where they are generated with virtual cameras. That is to say, the AP and LA DRRs are captured by two virtual cameras simulatively for example located at the particular spots toward to the vertebral body of interest of the patient 9000 along the AP and LA planes respectively. The DRRs correspond to the actual interoperative AP and lateral LA radiographs. The surgeon is presented with the DRRs and the actual radiographs and is asked to identify a common point in all images. This step provides a common point or position in the CT image data and the dynamic reference frame 1520A or patient space coordinates. Once the position and orientation of the patient 9000 in the three-dimensional data set and the dynamic reference frame coordinates are known, the method proceeds to the refinement step. After refinement, all of the systems involved are linked and known.

During the initialization step, the surgeon is asked to acquire AP and LA radiographs or radiographs along any two planes using the imaging device 1300. In a spinal procedure, the surgeon is prompted to identify the center of the vertebral body that the surgeon is interested in. Putting together all of this data, a good estimate of the orientation and the position is known and is used to calculate the DRRs that correspond closely to the actual radiographs for an initial two-dimensional to three-dimensional registration.

These DRRs are created by adopting the three-dimensional data from the CT scan combined with the information from the C-arm localization target.

The processor 1120 of the calculating device 1100 may access the three-dimensional image data set stored in the database 1200, and an AP virtual camera or an LA virtual camera corresponding to the three-dimensional image data set can be created by the processor 1120. Each of the virtual cameras has its own spatial parameters indicating the position and orientation corresponding to the body of interest in the three-dimensional image. Just like an actual camera, that the positions and orientations of the cameras corresponding to the target objective determines what images will be obtained. Therefore, changing the spatial parameter of a virtual camera will generate different reconstructed images from the three-dimensional image data set. In the present embodiment, the spatial parameter includes at least a distance parameter which indicates the distance from the target body of interest of the object 9000 to the virtual camera.

Preliminary Registration

In the preliminary registration step, software is used to provide matching algorithms that reprocess the preliminary two-dimensional to three-dimensional registration. The software is adopting to adjust the initial position and the orientation in a way as to minimize differences between the DRRs and the actual radiographs, thereby refining the registration. In the preliminary step, similarity or cost measures are implemented to identify how well the images match. An iterative preliminary algorithm adjusts the initial position and the orientation parameters simultaneously to maximize the similarity between the DRRs and the actual radiographs. The similarity or cost measures that are implemented are selected from known similarity and cost measures, such as normalized mutual information, mutual information, gradient difference algorithms, surface contour algorithms, pattern intensity algorithms, sum of squared differences, normalized cross-correlation, local normalized correlation, and correlation ratio. This procedure results in an efficient and accurate manner to provide two-dimensional to three-dimensional registration.

Subsequently, the processor 1120 of the calculating device 1100 may adjust the AP virtual camera or the LA virtual camera according to the distance parameter.

In some embodiments, the distance parameter is calculated according to the actual distance between two plain marks on an image of the two-dimensional image data set. For example, surgeons may be asked to manually make two marks on the single AP or LA two-dimensional image where they are interested in.

Figure 4:
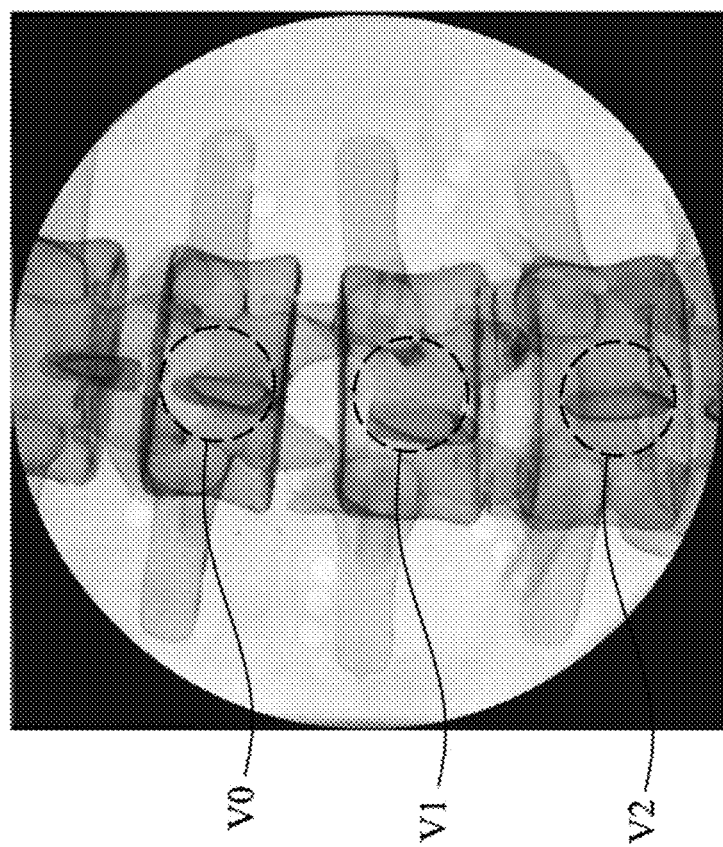
FIG. 4 depicts a schematic diagram of a portion of a body of interest according to one embodiment of the present disclosure.

In the present embodiment shown in FIG. 4, the object 9000 is a patient under a vertebral disorder, the surgeon may manually make two marks V0 and V1 on but not limited to the center of two target vertebral bodies of the object 9000 through the I/O interface 1130 in FIG. 2. As such, the distance between the marks V0 and V1 can be calculated by the processor 1120 of the calculating device 1100 with an imaging recognition technology. In some embodiments, the I/O interface 1130 can be electrically connected to any kind of input devices such as a mouse, a keyboard, and a touch panel for inputting.

Figure 5:
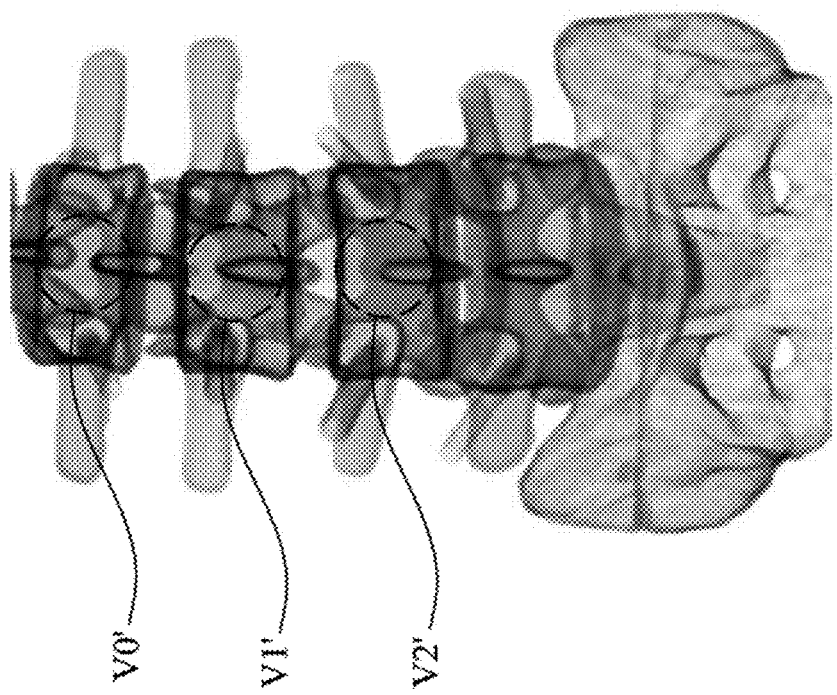
FIG. 5 depicts a schematic diagram of a portion of a body of interest according to one embodiment of the present disclosure.

As can be seen in FIG. 5, it is an AP digitally reconstructed radiograph (DRR) image generated by the processor 1120 with inputs combining the information of where the object 9000 was positioned or oriented corresponding to the imaging device 1300 during X-ray image acquisition.

Virtual camera in some embodiments is a modularized coding of the two-dimensional to three-dimensional registration program for generation of two-dimensional image from a three-dimensional volume at a parameter-driven position along with a parameter-driven orientation or perspective by the processor 1120 with known DRR algorithm.

Using this estimate of the orientation, the DRR image in FIG. 5 from the CT scan is created to correspond substantially to the actual interoperative radiograph in FIG. 4. By using the patient orientation information from the three-dimensional image data with the patient orientation information on the location of the imaging device 1300, this information is implemented in combination with known DRR algorithms to create the DRR. In other words, since it is known where the fluoroscopic scans were taken, and the right/left and AP directions of the CT data or any other directions are known, if a person takes a view through the three-dimensional volume data, along the direction of the fluoroscopic scan and an accurate DRR is obtained. The DRR is essentially a two-dimensional image taken from a three-dimensional volume where a view through the three-dimensional volume is generated by looking through three-dimensional volume from the proper orientation or perspective, to create a line for every voxel. Each line is considered to create a new voxel value, which generates the DRR.

However, the initial DRRs are not precisely matching with the AP and LA X-ray images. That is why there is a need to perform an alignment procedure during two-dimensional to three-dimensional registration.

The surgeons may manually make another two marks V0' and V1' on the target two vertebral bodies of the AP DRR image through the I/O interface 1130 in FIG. 2. As such, a distance between two marks V0' and V1' on the AP DRR image in FIG. 5 can be calculated by the processor 1120. Subsequently, if the distance between two marks V0 and V1 on the AP 2D image in FIG. 4 is, for example, 100 pixels, the processor 1120 may adjust the distance parameter of the AP virtual camera to regenerate an adjusted AP DRR image which has the distance between two marks V0' and V1' to be also 100 pixels. Therefore, the size of the target vertebral bodies shown on the AP DRR image in FIG. 5 is adjusted to be similar to the size of those shown on the AP 2D image in FIG. 4. In view of the above, it merely needs to focus on the distances regarding the marks on the AP 2D image in FIG. 4 and the AP DRR image in FIG. 5, and then adjusts the distances to be the same for alignment, and therefore, the alignment process can be very fast.

Figure 6:
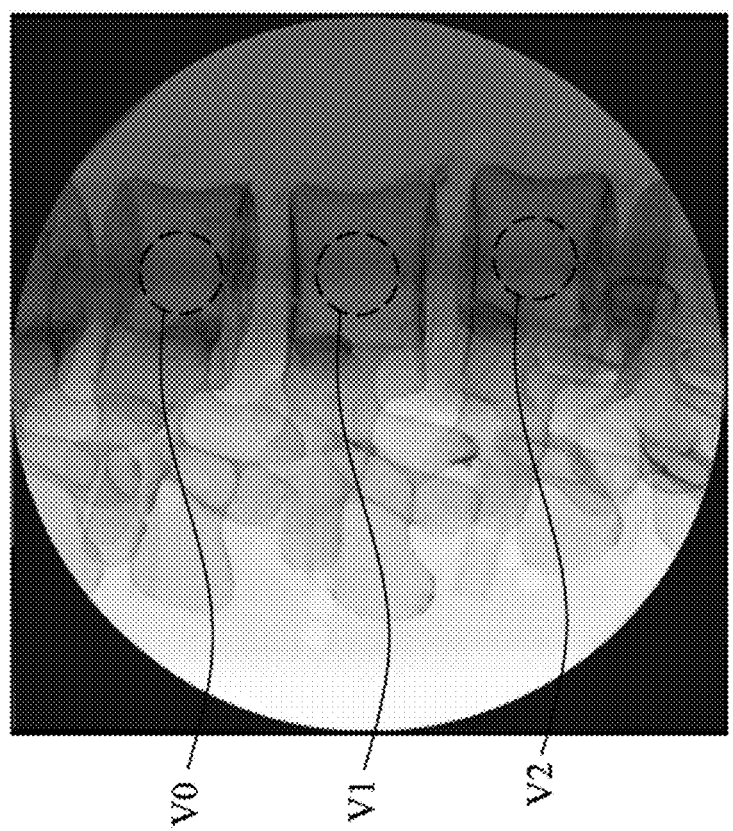
FIG. 6 depicts a schematic diagram of a portion of a body of interest according to one embodiment of the present disclosure.

Besides, in the present embodiment shown in FIG. 6, the surgeons may manually make marks V0 and V1 on two target vertebral bodies of the object 9000 through the I/O interface 1130 in FIG. 2. As such, the distance between the marks V0 and V1 can be calculated by the processor 1120 of the calculating device 1100 with an imaging recognition technology.

Figure 7:
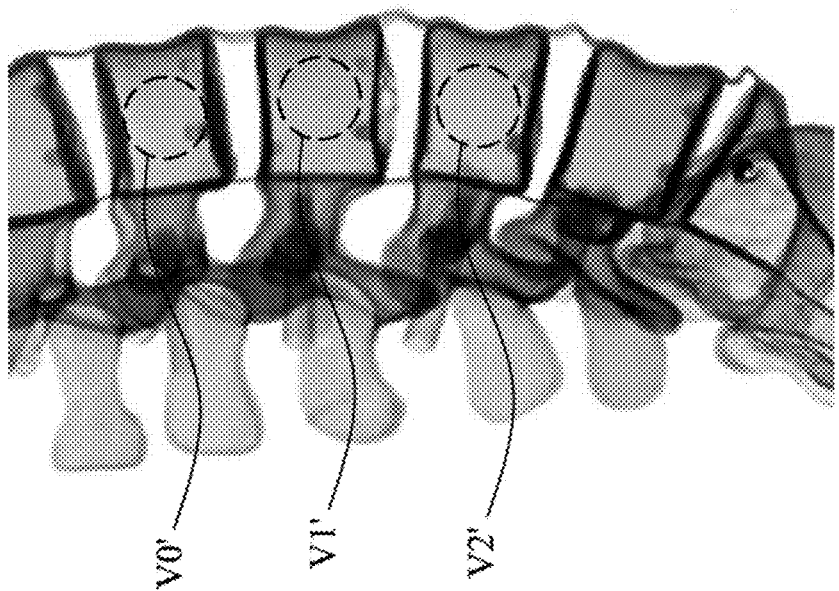
FIG. 7 depicts a schematic diagram of a portion of a body of interest according to one embodiment of the present disclosure.

As can be seen in FIG. 7, it is a LA DRR image generated by the processor 1120 with inputs combining the information of where the object 9000 was positioned or oriented corresponding to the imaging device 1300 during X-ray image acquisition. The surgeon may manually make two mark V0' and V1' on two target vertebral bodies of the object through the I/O interface 1130 in FIG. 2. As such, the distance between the marks V0' and V1' can be calculated by the processor 1120 of the calculating device 1100 with an imaging recognition technology. Subsequently, if the distance between two marks V0 and V1 on the LA 2D image in FIG. 6 is, for example, 100 pixels, the processor 1120 may adjust the distance parameter of the LA virtual camera to regenerate an adjusted LA DRR image which has the distance between two marks V0' and V1' to be also 100 pixels. Therefore, the size of the target vertebral bodies shown on FIG. 7 is adjusted to be similar to the size of those shown on the LA 2D image in FIG. 6. In view of the above, it merely needs to focus on the distances regarding the marks on the LA 2D image in FIG. 6 and the LA DRR image in FIG. 7, and then adjusts the distances to be the same for alignment, and therefore, the alignment process can be very fast.

In some embodiments the distance parameter is calculated according to a distance between an estimated position of an emitter and an estimated position of the body of interest. For example, as discussed above, the calibrator 1510 shown on the X-ray two-dimensional image generated by the imaging device 1300 in FIG. 1 can be used as a reference for the calculating device 1100 to calculate the estimated position of the X-ray emitter 1310. In addition, the estimated position of the object 9000 can be calculated by the calculating device 1100 according to the X-ray image showing the calibrators 1510 and the estimated position of the X-ray emitter 1310. Thereafter, if the estimated position of the X-ray emitter 1310 and the estimated position of the object 9000 are obtained, the distance between the X-ray emitter 1310 and the estimated position of the object 9000 is able to be calculated by the calculating device 1100.

Figure 8:
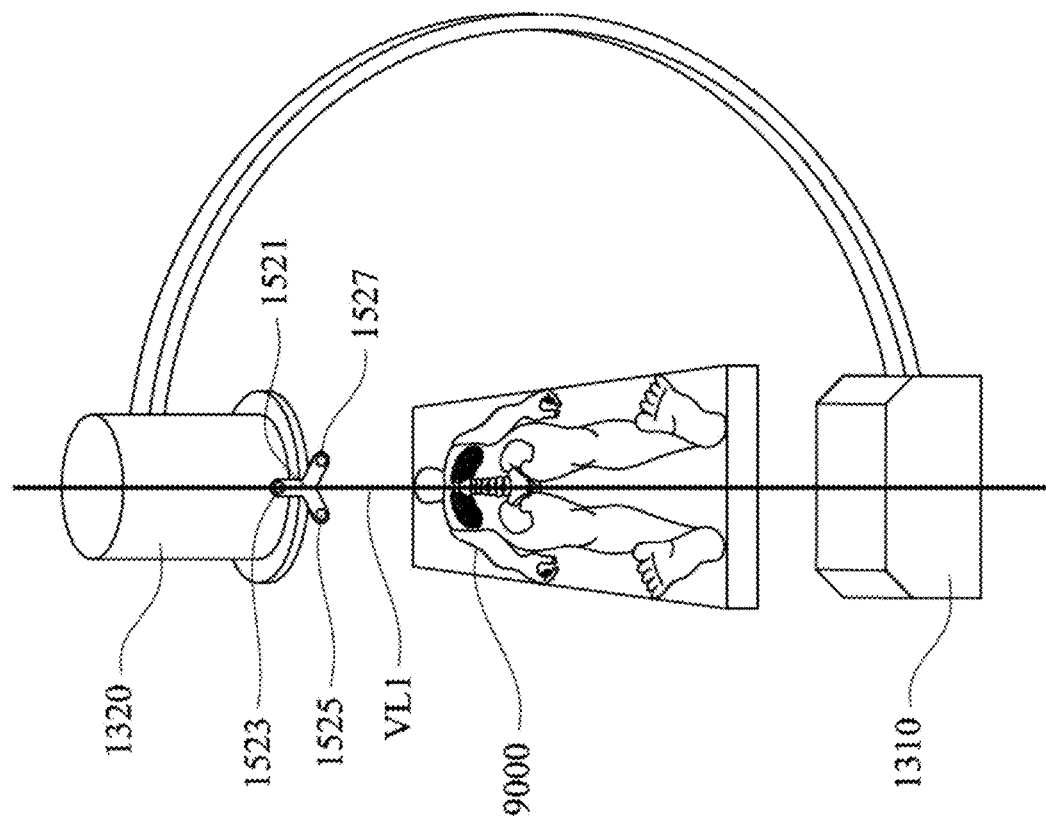
FIG. 8 depicts a schematic diagram of operations of the C-arm device shown in FIG. 1 according to one embodiment of the present disclosure.
Figure 9:
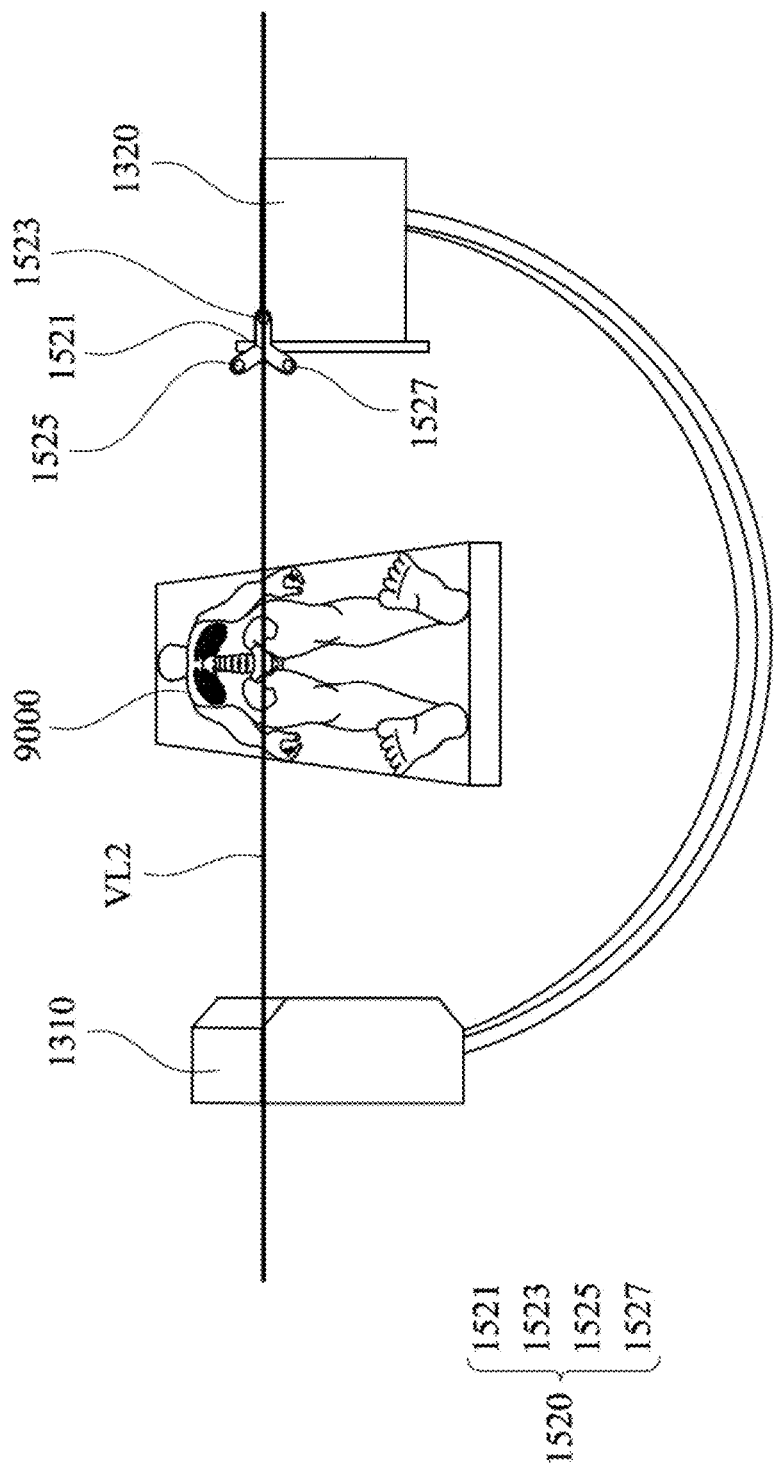
FIG. 9 depicts a schematic diagram of operations of the C-arm device shown in FIG. 1 according to one embodiment of the present disclosure.

In some embodiments, the estimated position of the emitter is calculated according to the two-dimensional image data set, and the estimated position of the body of interest is at a position at which a first virtual line and a second virtual line are the closest. For example, the calculating device 1100 in FIG. 2 may obtain the X-ray images from the imaging device 1300. As discussed above, the X-ray images from the imaging device 1300 may include the calibrator 1510 in FIG. 1. Therefore, the calculating device 1100 may calculate the estimated position of the X-ray emitter 1310 according to the X-ray image including the calibrator 1510. Referring to FIG. 8, there is a first virtual line VL1 which is generated between the estimated position of the X-ray emitter 1310 and the calibrator 1510. Referring to FIG. 9, there is a second virtual line VL2 which is generated between the estimated position of the X-ray emitter 1310 and the calibrator 1510. If the first virtual line VL1 in FIG. 8 and the second virtual line VL2 in FIG. 9 are located in the same coordinate system, the estimated position of the object 9000 is determined at a position at which the first virtual line VL1 and the second virtual line VL2 are the closest.

In some embodiments, the two-dimensional image data set includes first and second two-dimensional images, the first virtual line is generated between the estimated position of the emitter and a central point of at least two reflectors which are radiated when the first two-dimensional image data set is captured, the second virtual line is generated between the estimated position of the emitter and the central point of the at least two reflectors which are radiated when the second two-dimensional image data set is captured.

For example, the X-ray images from the imaging device 1300 in FIG. 1 include the AP 2D image and the LA 2D image of the object 9000. Referring to FIG. 8, the first virtual line VL1 is generated between the estimated position of the X-ray emitter 1310 and a central point 1521 of reflectors 1523, 1525, 1527 which can be related to the dynamic reference frame 1520A in FIG. 1 and are obtained by the optical tracker 1400. Referring to FIG. 9, the second virtual line VL2 is generated between the estimated position of the X-ray emitter 1310 and a central point 1521 of reflectors

1523, 1525, 1527 which can be related to the dynamic reference frame 1520A in FIG. 1 and obtained by the optical tracker 1400. It is noted that the central point 1521 can be an original point of the calibrator coordinate constructed by the reflectors 1523, 1525, 1527, and the location of the central point 1521 in not limited to the physical center of the reflectors 1523, 1525, 1527.

Referring to both FIG. 2 and FIG. 3, in operation, the step 2200 is performed by the processor 1120 to rotate the first virtual camera according to an angle difference between a first vector and a second vector, wherein the first vector is calculated from two spatial marks in the three-dimensional image data set, and the second vector is calculated from two first plain marks in the two-dimensional image data set.

For example, the first vector is calculated from two spatial marks in the three-dimensional image generated by the AP virtual camera with proper DDR algorithm. Referring to FIG. 4, the second vector is calculated from two plain marks V0 and V1 on the AP two-dimensional image. When the first vector and the second vector are obtained, the processor 1120 may calculate an angle difference between the first vector and the second vector. Subsequently, the processor 1120 can rotate the AP virtual camera according to the angle difference. Therefore, the orientation or perspective of the AP virtual camera is adjusted to be similar or identical in the best to that of the X-ray emitter 1310 of the imaging device 1300 along the AP plain in FIG. 4. This step is executed by the calculating device 1100 to adjust or modify the orientation or perspective parameter of the DRR algorithm so as to generate an adjusted or modified DRR image which is more similar or identical in the best to the AP two-dimensional X-ray image. In view of the above, the vertebral bodies in the AP two-dimensional image and the AP DRR image can be adjusted to be identical, and the elevation angles regarding the LA two-dimensional image and the LA DRR image can be adjusted to be similar.

Furthermore, the first vector is calculated from two spatial marks in the three-dimensional image generated by the LA virtual camera with proper DDR algorithm. Referring to FIG. 6, the second vector is calculated from two plain marks V0 and V1 on the LA two-dimensional image. When the first vector and the second vector are obtained, the processor 1120 may calculate an angle difference between the first vector and the second vector. Subsequently, the processor 1120 can rotate the LA virtual camera according to the angle difference. Therefore, the orientation or perspective of the LA virtual camera is adjusted to be similar or identical in the best to that of the X-ray emitter 1310 of the imaging device 1300 along the LA plain in FIG. 6. This step is executed by the calculating device 1100 to adjust or modify the orientation or perspective parameter of the DRR algorithm so as to generate an adjusted or modified DRR image which is more similar or identical in the best to the LA two-dimensional X-ray image. In view of the above, the vertebral bodies in the LA two-dimensional image and the LA DRR image can be adjusted to be identical, and the elevation angles regarding the AP two-dimensional image and the AP DRR image can be adjusted to be similar.

In some embodiments, the two-dimensional image data set includes a first two-dimensional image, the first vector is calculated from the two spatial marks in the three-dimensional image data set generated by the first virtual camera, and the second vector is calculated by the two first plain marks in the first two-dimensional image data. For example, the two-dimensional image data set includes the AP two-dimensional image in FIG. 4. The first vector is calculated from two spatial marks in the three-dimensional image data set generated by the AP virtual camera. The second vector is calculated by two plain marks V0 and V1 in the AP two-dimensional image in FIG. 4.

In some embodiments, the two-dimensional image data set includes a second two-dimensional image, and the second vector is calculated from the two second plain marks in the second two-dimensional image data. For example, the two-dimensional image data set includes the LA two-dimensional image in FIG. 6. The first vector is calculated from two spatial marks in the three-dimensional image data set generated by the LA virtual camera. The second vector is calculated from the two plain marks V0 and V1 in the LA two-dimensional image in FIG. 6.

Reference is now made to both FIG. 2 and FIG. 3. In operation, the step 2300 is performed by the processor 1120 to rotate the first virtual camera according to an angle which is corresponding to a maximum similarity value of a plurality of similarity values calculated in accordance with reconstructed images of the three-dimensional image data set which includes one generated by the first virtual camera and the others generated by other virtual cameras with different angles or different pixels from the one generated by the first virtual camera and the two-dimensional image data set for implementing in the two-dimensional image data set to the three-dimensional image data set registration of the navigation system 1000 after adjusting and rotating.

For example, first, a few LA DRR images are generated by adjusting the pre-determined position and/or orientation of the LA virtual camera in the coordinate system of the three-dimensional image data set. The pre-determined position and/or orientation of the LA virtual camera can be chosen by the surgeon in accordance with the volume of interest in the three-dimensional data set.

The LA DRR images can be generated by taking the pre-determined position and/or orientation of the LA virtual camera as the center and then rotating its roll angle in a range from −20 degrees to 20 degrees and/or moving its position in a range from −15 pixels to 15 pixels for DRR generation. Since different LA DRR images have different contents, a plurality of similarity values can be calculated in accordance with the LA DRR images and the pre-determined LA two-dimensional image, which is chosen by the surgeon in accordance with the region of interest corresponding to the volume of interest. Then, the maximum similarity value will be obtained from the plurality of similarity values. For a higher alignment between the two-dimensional and DRR image, the current position and/or orientation of the LA virtual camera will be adjusted according to the pixel and roll angle corresponding to the maximum similarity value. In other words, the vertebras in the LA DRR image are adjusted to be similar to the vertebras of the LA two-dimensional image. The AP virtual camera regarding each vertebral bodies of the object 9000 can be adjusted according to LA virtual camera in accordance with corresponding vertebral bodies of the object 9000.

In addition, a few AP DRR images are generated by adjusting the pre-determined position and/or orientation of the AP virtual camera in the coordinate system of the three-dimensional image data set. The pre-determined position and/or orientation of the AP virtual camera can be chosen by the surgeon in accordance with the volume of interest in the three-dimensional data set.

The AP DRR images can be generated by taking the pre-determined position and/or orientation of the AP virtual camera as the center and then rotating its azimuth angles in a range from −15 degrees to 15 degrees and/or moving its position in a range from −15 pixels to 15 pixels for DRR generation. Since different AP DRR images have different contents, a plurality of similarity values can be calculated in accordance with the AP DRR images and the pre-determined AP two-dimensional image, which is chosen by the surgeon in accordance with the region of interest corresponding to the volume of interest. Then, the maximum similarity value will be obtained from the plurality of similarity values. For a higher alignment between the two-dimensional and DRR image, the current position and/or orientation, of the AP virtual camera will be adjusted according to the pixel and azimuth angle corresponding to the maximum similarity value. In other words, the vertebras in the AP DRR image are adjusted to be similar to the vertebras of the AP 2D image. The LA virtual camera regarding each vertebral bodies of the object 9000 can be adjusted according to AP virtual camera in accordance with corresponding vertebral bodies of the object 9000.

In some embodiments, an adjusted first virtual camera is generated after the rotation of the first virtual camera. The processor 1120 is used to perform a step of rotating the adjusted first virtual camera according to the angle which is corresponding to an adjusted maximum similarity value of the plurality of similarity values calculated in accordance with adjusted reconstructed images which includes one generated by the adjusted first virtual camera and the others generated by other virtual cameras with different angles from the one generated by the adjusted first virtual camera and the two-dimensional image data set.

For example, adjusted AP virtual camera or adjusted LA virtual camera are generated after the rotation of the AP virtual camera or the LA virtual camera. The adjusted LA DRR images are generated by the adjusted LA virtual camera with roll angles in a range from −20 degrees to 20 degrees and/or moving its position in a range from −15 pixels to 15 pixels far DRR generation. Since different LA DRR images have different contents, a he plurality of similarity values can be calculated in accordance with the adjusted LA DRR images and the pre-determined LA two-dimensional imager which is chosen by the surgeon in accordance with the region of interest corresponding to the volume of interest. Then, the adjusted maximum similarity value will be obtained from the plurality of similarity values. For a higher alignment between the two-dimensional and DRR image, the current position and/or orientation of the LA virtual camera will he adjusted according to the pixel and roll angle corresponding to the maximum similarity value. In other words, the vertebras in the LA DRR image are adjusted to be similar to the vertebras of the LA two-dimensional image.

Besides, the adjusted AP DRR images are generated by the adjusted AP virtual camera with azimuth angles in a range from −15 degrees to 15 degrees and/or moving its position in a range from −15 pixels to 15 pixels for DRR generation. Since different APDRR images have different contents, a be plurality of similarity values can be calculated in accordance with the adjusted AP DRR images and the AP two-dimensional image, which is chosen by the surgeon in accordance with the region of interest corresponding to the volume of interest. Then, the adjusted maximum similarity value will be obtained from the plurality of similarity values. For a higher alignment between the two-dimensional and DRR image, the current position and/or orientation of the AP virtual camera will be adjusted according to the pixel and roll angle corresponding to the maximum similarity value. In other words, the vertebras in the AP DRR image are adjusted to be similar to the vertebras of the AP two-dimensional image.

It is noted that, the present disclosure is not limited to the structures and the operations as shown in FIG. 2 to FIG. 9, and it is merely an example for illustrating one of the implements of the present disclosure.

In some embodiments, the processor 1120 is used to perform a step of adjusting the first virtual camera of the plurality of virtual cameras corresponding to the three-dimensional image data set according to a matrix corresponding to the two-dimensional image data set. Far example, both of the AP two-dimensional image and the LA two-dimensional image from the imaging device 1300 in FIG. 1 includes the calibrator 1510. The processor 1120 may calculate the matrix which functions to transform the coordinate system of the AP two-dimensional image to the coordinate system of the LA two-dimensional image by the given parameter of the calibrator 1510. Therefore, the matrix corresponding to the relation between the AP two-dimensional image and the LA two-dimensional image is obtained. Subsequently, the processor 1120 may adjust the AP virtual camera or the LA virtual camera according to the matrix, such that the relation between the AP virtual camera and the LA virtual camera is similar to the relation between the AP two-dimensional image and the LA two-dimensional image.

2D to 3D Registration

Once the initialization alignment as the first stage is completed, the navigation system 1000 proceeds to establish the relation between the three-dimensional image data set stored in the database 1200 and the X-ray two-dimensional images of the two-dimensional image data set shown on the monitor of the imaging device 1300 or stored in the database 1200, which will be described below.

Figure 10:
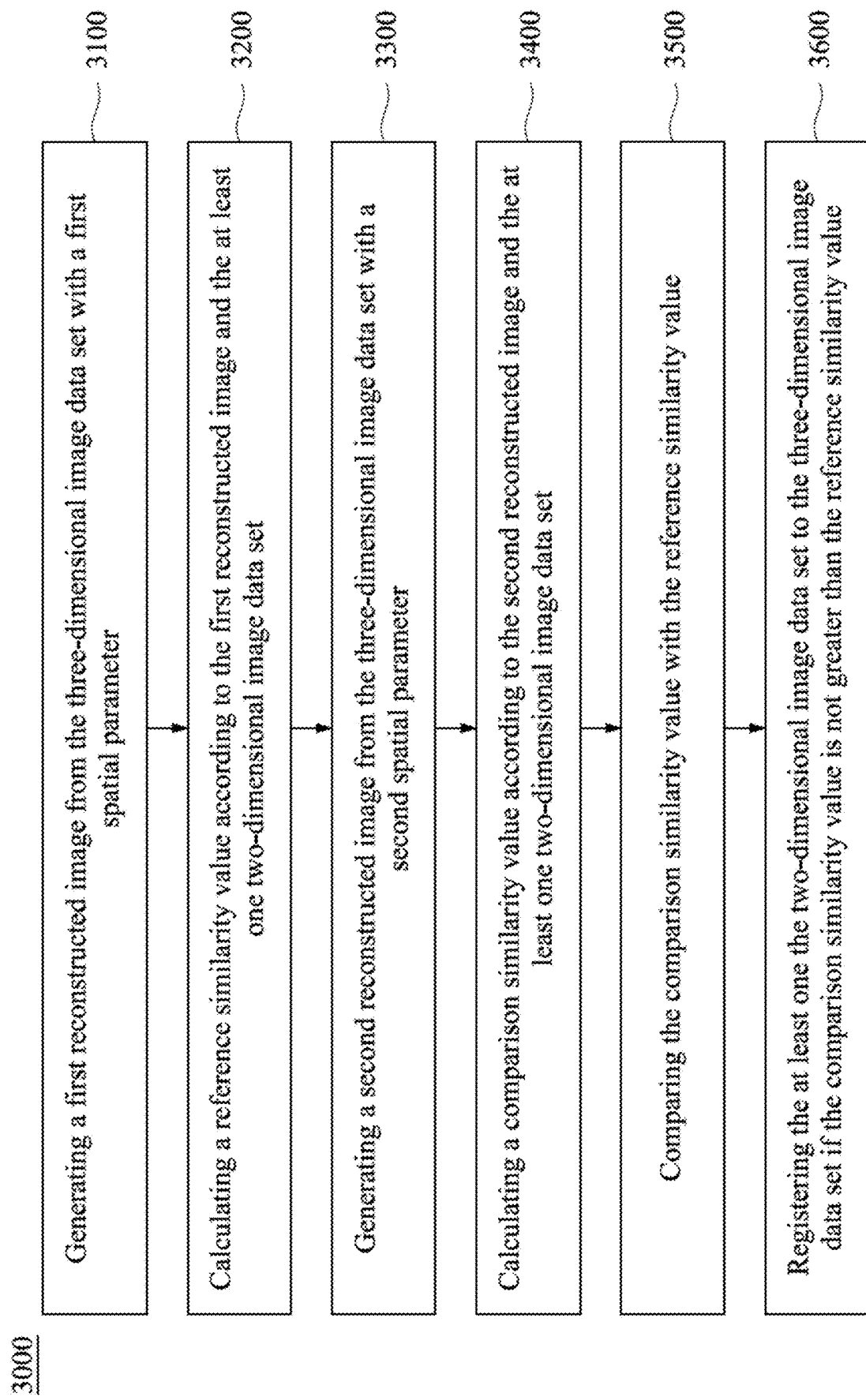
FIG. 10 depicts a flow diagram of a method for registering a two-dimensional image data set with a three-dimensional image data set of a body of interest according to one embodiment of the present disclosure.

FIG. 10 depicts a flow diagram of a method for registering at least one two-dimensional image of the two-dimensional image data set of a body of interest with a three-dimensional image data set of the same body of interest according to one embodiment of the present disclosure. Reference is now made to both FIG. 2 and FIG. 10. In operation, the step 3100 is performed by the processor 1120 to generate a first reconstructed image from the three-dimensional image data set with a first spatial parameter.

For example, the processor 1120 of the calculating device 1100 may access the database 1200 and simulate a virtual camera corresponding to the three-dimensional image data set with the first spatial parameter so as to generate a first DRR image. In the present embodiment, the virtual camera has been aligned in advance (through the initialization alignment and/or other one or more adjustment means of facilitating two-dimensional to three-dimensional registration), but, however, the virtual camera in other embodiment of the present invention hasn't been adjusted through the initialization alignment and/or other one or more adjustment means.

Referring to both FIG. 2 and FIG. 10, operation, the step 3200 is performed by the processor 1120 to calculate a reference similarity value according to the first reconstructed image and the at least one two-dimensional image data set. For example, the processor 1120 of the calculating device 1100 may calculate the reference similarity value according to the first DRR image and the 2D image data.

Reference is now made to both FIG. 2 and FIG. 10. In operation, the step 3300 is performed by the processor 1120 to generate a second reconstructed image from the three-dimensional image data set with a second spatial parameter. For example, the processor 1120 of the calculating device 1100 may access the database 1200 and simulate the virtual camera corresponding to the 3D image data set with the second spatial parameter so as to generate a second DRR image.

Referring to both FIG. 2 and FIG. 10, in operation, the step 3400 is performed by the processor 1120 to calculate a comparison similarity value according to the second reconstructed image and the at least one two-dimensional image data set. For example, the processor 1120 of the calculating device 1100 may calculate the comparison similarity value according to the second DRR image and the 2D image data.

Reference is now made to both FIG. 2 and FIG. 10. In operation, the step 3500 is performed by the processor 1120 to compare the comparison similarity value with the reference similarity value. For example, the processor 1120 of the calculating device 1100 may compare the comparison similarity value with the reference similarity value.

Referring to both FIG. 2 and FIG. 10, operation, the step 3600 is performed by the processor 1120 to register the at least one the two-dimensional image data set to the three-dimensional image data set if the comparison similarity value is not greater than the reference similarity value for computer-assisted surgical navigation based on the two-dimensional image data set and the three-dimensional image data set after registering. For example, if the comparison similarity value is not greater than the reference similarity value, it means that the second DRR image is aligned with the 2D image data. Therefore, the processor 1120 of the calculating device 1100 may register the 2D image data set from the imaging device 1300 to the 3D image data set stored in the database 1200. Thereafter, since the 2D image data set from the imaging device 1300 is registered to the 3D image data set stored in the database 1200, the method 3000 in FIG. 10 of the present disclosure can be used for computer-assisted surgical navigation based on the two-dimensional image data set and the three-dimensional image data set.

It is noted that, the present disclosure is not limited to the operations as shown in FIG. 10, and it is merely an example for illustrating one of the implements of the present disclosure. In addition, the method 3000 in FIG. 10 can be performed by the processor 1120 to register the two-dimensional image data set including an AP two-dimensional image and a LA two-dimensional image to the three-dimensional image data set from which an AP DRR image and a LA DRR image derived.

In some embodiments, the steps of generating the first reconstructed image or the second reconstructed image from the three-dimensional image data set with the first reconstructed image or the second reconstructed image which are performed by the processor comprise: positioning a virtual camera corresponding to a three-dimensional subject composed in accordance with the first reconstructed image or the second reconstructed image so as to capture the first reconstructed image or the second reconstructed image of the three-dimensional subject by the virtual camera.

For example, the three-dimensional image data set may be a volume of voxels obtained after the CT scanning of the object 9000 including the body of interest. The volume of voxels can be presented in a way of volume rendering and then a three-dimensional subject, also known as a three-dimensional model, of the body of interest can be shown on a display and stored in the database 1200 simultaneously. The processor 1120 may access the database 1200 for the three-dimensional model, and also determining the position and orientation of a virtual camera corresponding to the three-dimensional model with the spatial parameter given to the virtual camera. Once the virtual camera is set, the processor 1100 is able to acquire one or a plurality of two-dimensional images as the first DRR image or the second DRR image by the DRR algorithm in the art.

In some embodiments, the virtual camera is defined by a modularized function. The modularized function includes an algorithm and an equation. In some embodiments, the virtual camera is simulated by but not limited to a ray projection volume rendering.

In the initialization alignment, the virtual camera will be adjusted to preset an initial spatial parameter including a position and/or an orientation of the virtual camera so as to improve the efficiency and enhance the precision of the navigation system 1000. However, for medical purpose there are still insufficiency, and therefore, the adjusted virtual camera after performing the initialization alignment should be further refined in the two-dimensional to three-dimensional registration for becoming more accurate. In some embodiments, each of the first spatial parameter and the second spatial parameter is used to define a position and/or an orientation of the adjusted virtual camera corresponding to the three-dimensional subject or the three-dimensional subject corresponding to the adjusted virtual camera. As mentioned above, the adjusted virtual camera should be further refined, and the way to refine the adjusted virtual camera is to adjust spatial parameter including a position and/or an orientation of the adjusted virtual camera. For example, each of the first spatial parameter and the second spatial parameter is used to define a position and/or an orientation of the adjusted virtual camera corresponding to the three-dimensional subject or the three-dimensional subject corresponding to the adjusted virtual camera.

In some embodiments, each of the first spatial parameter and the second spatial parameter individually comprises one of a position, an orientation, and a parameter comprising the position and the orientation. For example, the first spatial parameter can be a position, an orientation, or a parameter including the position and the orientation, and the second spatial parameter can be a position, an orientation, and a parameter including the position and the orientation.

In some embodiments, each of the comparison similarity value and the reference similarity value is calculated by but not limited to local normalized correlation (LNC), sum of squared differences (SSD), normalized cross-correlation (NCC), or correlation ratio (CR).

In some embodiments, the three-dimensional image data set (e.g., the 3D image data set stored in the database 1200 in FIG. 1) is generated by one of a magnetic resonance imaging (MRI) device, an iso-centric imaging fluoroscopic imaging device, an O arm device, a bi-plane fluoroscopy device, a computed tomography (CT) device, a multi-slice computed tomography (MSCT) device, a high frequency ultrasound (HIFU) device, an optical coherence tomography (OCT) device, an intra-vascular ultrasound (IVUS) device, a 3D or 4D ultrasound device, and an intraoperative CT device.

In some embodiments, the two-dimensional image data set is generated by one of a C-arm fluoroscopic imaging device, a magnetic resonance imaging (MRI) device, an iso-centric C-arm fluoroscopic imaging device, an O-arm device, a hi-plane fluoroscopy device, a computed tomography (CT) device, a multi-slice computed tomography (MSCT) device, a high frequency ultrasound (HIFU) device, an optical coherence tomography (OCT) device, an intra-vascular ultrasound (IVUS) device, a two-dimensional, three-dimensional or four-dimensional ultrasound device, and an intraoperative CT device.

In some embodiments, the first spatial parameter is generated in accordance with a spatial relationship between at least one maker on a two-dimensional image capturing device and the body of interest. As mentioned above, the virtual camera will be adjusted to preset the initial spatial parameter in the initialization alignment so as to improve the efficiency and enhance the precision of the navigation system 1000. and the adjusted spatial parameter after the initialization alignment is subsequently used as the first spatial parameter in this two-dimensional to three-dimensional registration. For example, the first spatial parameter is generated in accordance with a spatial relationship between the calibrator 1510 on the X-ray receiver 1320 and the object 9000 in FIG. 1.

In some embodiments, the first spatial parameter is a spatial parameter which has a maximum similarity among a plurality of similarities generated in a previous comparison step. For example, the comparison steps may be performed many times and each comparison steps will generate a similarity. The first spatial parameter is obtained by finding the parameter that has the maximum similarity among the plurality of similarities.

In some embodiments, the adjusted virtual camera in the beginning of the two-dimensional to three-dimensional registration has the first spatial parameter including the first distance and/or the first orientation. When the two-dimensional to three-dimensional registration starts, the adjusted virtual camera will be moved from the first spatial parameter to the second spatial parameter including the second distance and/or the second orientation. Therefore, the second spatial parameter is different from the first spatial parameter aspect of defining a distance and/or an orientation of the corresponding virtual camera corresponding to the three-dimensional image data set (e.g., the three-dimensional image data set stored in the database 1200 in FIG. 1). In more detail, since the adjusted virtual camera described in the present embodiment is a modularized function including an algorithm, equation and one or a plurality of parameters involved therein, the processor 1100 can use the parameters and then stimulate the adjusted virtual cameras at particular locations in the coordinate system of the three-dimensional image data set.

In some embodiments, the processor 1120 is further used to perform the following steps: generating a third reconstructed image from the three-dimensional image data set with a third spatial parameter if the comparison similarity value is greater than the reference similarity value; calculating a second comparison similarity value according to the third reconstructed image and the at least one two-dimensional image data set; comparing the second comparison similarity value with the reference similarity value; and registering the at least one the two-dimensional image data set to the three-dimensional image data set if the second comparison similarity value is not greater than the reference similarity value.

For example, if the comparison similarity value is greater than the reference similarity in the previous comparison, the processor 1120 of the calculating device 1100 may access the database 1200 and simulate the adjusted virtual camera corresponding to the 3D image data set at a third location so as, to generate a third DRR image.

Besides, the processor 1120 of the calculating device 1100 may calculate the second comparison similarity value according to the third AP and/or LA DRR images and the corresponding AP and/or LA two-dimensional images of the two-dimensional image data set.

In addition, the processor 1120 of the calculating device 1100 may compare the second comparison similarity value with the reference similarity value.

Furthermore, if the second comparison similarity value is not greater than the reference similarity value, it means that the third AP and/or LA DRR images are aligned with the corresponding AP and/or LA two-dimensional images of the two-dimensional image data set. Then, the two-dimensional image data set acquired by the imaging device 1300 in real-time operation can be considered being registered to the three-dimensional image data set acquired previously and pre-stored in the database 1200.

Figure 11:
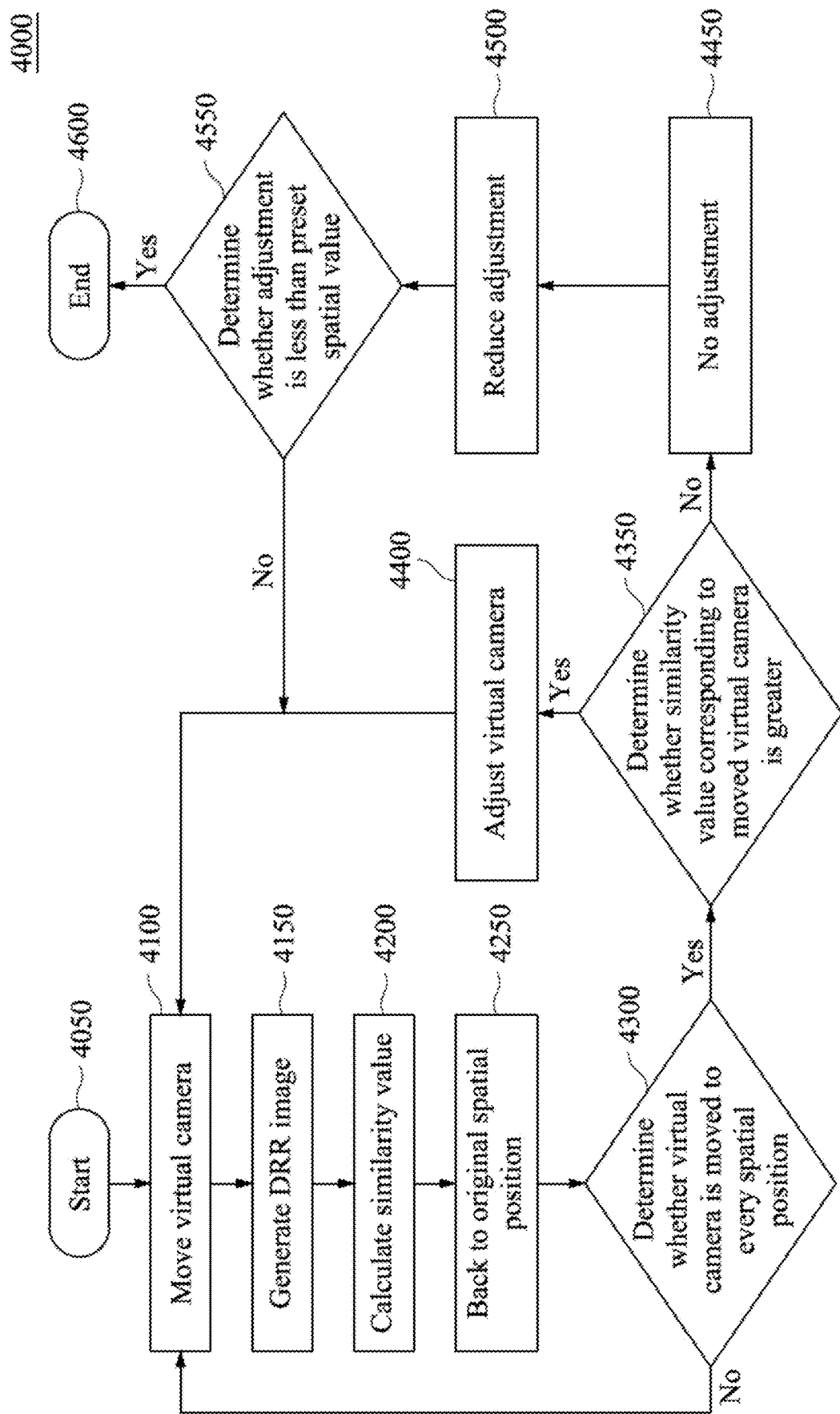
FIG. 11 depicts a flow diagram of a method for registering a two-dimensional image data set with a three-dimensional image data set of a body of interest according to one embodiment of the present disclosure.

FIG. 11 depicts a flow diagram of a method 4000 for registering a two-dimensional image data set of a body of interest with a three-dimensional image data set of the body of interest according to one embodiment of the present disclosure. Reference is now made to both FIG. 2 and FIG. 11. In operation, the step 4100 is performed by the processor 1120 to simulatively move the adjusted virtual camera from an original or a former spatial position of the coordinate system of the three-dimensional image data set to a first spatial position, and the step 4150 is performed by the processor 1120 to generate a first DRR image, also known as a first reconstructed image, corresponding to the first spatial position of the first virtual camera. The step 4200 is then performed by the processor 1120 to calculate a first similarity value according to the first. DRR image and a two-dimensional image, which can be AP or LA two-dimensional image, generated from the imaging device 1300, and step 4250 is performed by the processor 1120 to move the adjusted virtual camera back to the original spatial position.

Subsequently, the step 4300 is performed by the processor 1120 to determine whether the adjusted virtual camera is moved from the original spatial position to every spatial position. For example, the adjusted virtual camera can be moved from the original spatial position to a first spatial position (e.g., moved from (0,0) to (1,0) in the Cartesian coordinate system), then moved from the original spatial position to a second spatial position (e.g., moved from (0,0) to (−1,0) in the Cartesian coordinate system), and so on. The movement of the adjusted virtual camera is preset according to actual requirements. If it is determined that the adjusted virtual camera is not moved to every spatial position, the method 4000 is back to the step 4100 so as to move the adjusted virtual camera to another spatial position such as a second spatial position. The steps 4150, 4200 are then performed by the processor 1120 to generate another DRR image such as a second DRR image, and calculate another similarity value such as a second similarity value. Thereafter, the step 4250 is performed by the processor 1120 to move the adjusted virtual camera back to the original spatial position.

If it is determined that the adjusted virtual camera is moved to every spatial position, the method 4000 proceeds to the step 4350. The step 4350 is then performed by the processor 1120 to determine whether a similarity value corresponding to the moved virtual camera is greater. If it is determined that similarity value corresponding to the moved virtual camera is greater, it means that the DRR image generated by the adjusted virtual camera at the latter position is more similar to the two-dimensional image than the DRR image generated by the adjusted virtual camera at the original or former spatial position. Therefore, the step 4400 is then performed by the processor 1120 to adjust the adjusted virtual camera from the original or former spatial position to the latter spatial position. The original spatial position described in the present embodiment represents a position at which the adjusted virtual camera is located by the processor 1120 in the very beginning, and additionally the former spatial position represents at which the adjusted virtual camera is relocated after an adjustment which may result from any of or any combination of the abovementioned alignment or registration processes such as the initialization alignment.

After the step 4400 is performed, the method 4000 is back to step 4100. The steps 4100, 4150, 4200, 4250, 4300, and 4350 are then performed by the processor 1120. Referring to the step 4350, if it is determined that the similarity value corresponding to the adjusted virtual camera at the latter position is not greater than any one of the former similarity values, the method 4000 proceeds to the step 4450.

After the step 4450 is performed, the step 4500 is performed by the processor 1120 to reduce the adjustment. For example, if the previous adjustment is to move the adjusted virtual camera for 1 mm from the former position in the coordinate system of the three-dimensional subject presented by the three-dimensional image data set, the step 4500 is performed by the processor 1120 to reduce the adjustment to 0.5 mm. Thereafter, the step 4550 is performed by the processor 1120 to determine whether the adjustment is less than a preset spatial value, which is for example 0.75 mm. If it is determined that the adjustment is not less than the preset spatial value, the method 4000 is back to the step 4100.

If it is determined that the adjustment is less than the preset spatial value, it means that the DRR image is adequately aligned with the two-dimensional image. Therefore, it can define that the two-dimensional image data set from the imaging device 1300 has been registered to the three-dimensional image data set pre-stored in the database 1200.

In some embodiments, if a difference between the first spatial parameter and the second spatial parameter is not greater than a preset spatial value, registering the two-dimensional image data set to the three-dimensional image data set. For example, as can be seen in the step 4550 in FIG. 11, the difference between the first spatial position and the second spatial position is the adjustment in the step 4550. If the adjustment between the first spatial position and the second spatial position is not greater than the preset spatial value, it means that the DRR image is aligned with the two-dimensional image data. For example, the present spatial value can be 0.01 mm. If the adjustment is not greater than 0.01 mm. it means that the DRR image is already aligned with the two-dimensional image data. Therefore, the processor 1120 of the calculating device 1100 may register the 2D image data set from the imaging device 1300 to the 3D image data set stored in the database 1200.

It is noted that, the present disclosure is not limited to the operations as shown in FIG. 11, and it is merely an example for illustrating one of the implements of the present disclosure.

Figure 12:
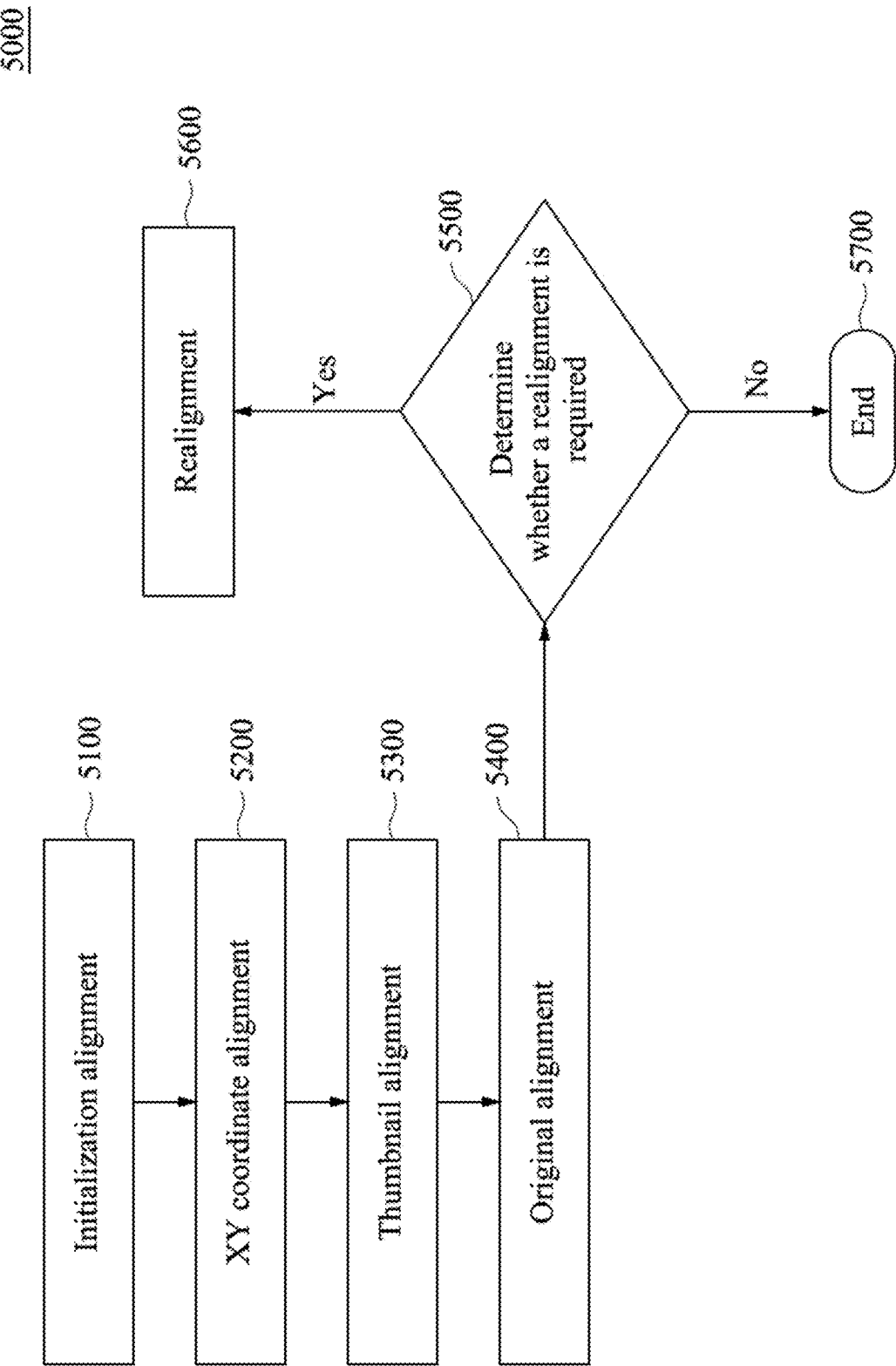
FIG. 12 depicts a flow diagram of a method for registering two-dimensional image data set with a three-dimensional image data set of a body of interest according to one embodiment of the present disclosure.

FIG. 12 depicts a flow diagram of a method 5000 for registering a two-dimensional image data set with a three-dimensional image data set of a body of interest according to one embodiment of the present disclosure. Reference is now made to both FIG. 2 and FIG. 12. In operation, the step 5100 is performed by the processor 1120 to execute an initialization alignment process to the navigation platform 1000 so as to enhance the precision of the navigation platform 1000.

The step 5200 is performed by the processor 1120 to execute a XY location alignment process to preset the XY location of the adjusted virtual camera corresponding to the three-dimensional image data set pre-stored in the database 1200 of the navigation platform 1000.

The step 5300 is performed by the processor 1120 to execute a contracted drawing alignment to the adjusted virtual camera corresponding to the three-dimensional image data set pre-stored in the database 1200 of the navigation platform 1000 preliminarily.

The step 5400 is performed by the processor 1120 to execute an original drawing alignment to the adjusted virtual camera corresponding to the three-dimensional image data set pre-stored in the database 1200 of the navigation platform 1000.

It is noted that a flow diagram of the XY coordinate alignment in the step 5200, the thumbnail alignment in the step 5300, and the original alignment in the step 5400 is shown in FIG. 11. The difference is that the XV coordinate alignment is focused on alignment of the images on the X coordinate and the Y, the thumbnail alignment uses preview or zoom-out images to achieve a quick alignment, and the original alignment is performed to further improve the alignment after the preview alignment.

The step 5500 is performed by the processor 1120 to determine whether realignment is required. The realignment process is required if an error or alignment failure determined by the processor 1120 or a judgment from a surgeon. For example, while the difference is always greater than a preset value after several calculation cycles, and the method 5000 proceeds to the step 5600 for realignment. On the contrary, the method 5000 proceeds to the step 5700 if the alignment is adequate and no realignment process is needed. In that situation, the whole alignment process in FIG. 12 is completed.

In some embodiments, the navigation system 1000 uses low-resolution images for preliminary alignment with the two-dimensional images before stimulation adjusted virtual cameras for generating the first and the second reconstructed images. The low-resolution format used herein is to reduce interference or noise signal between two similar images and therefore facilitate the preliminary alignment. As in the step 5300 of the method 5000, the DRR images used in the thumbnail alignment are low-resolution images.

Realignment

It is noted that, the present disclosure is not limited to the operations as shown in FIG. 12, and it is merely an example for illustrating one of the implements of the present disclosure.

Figure 13:
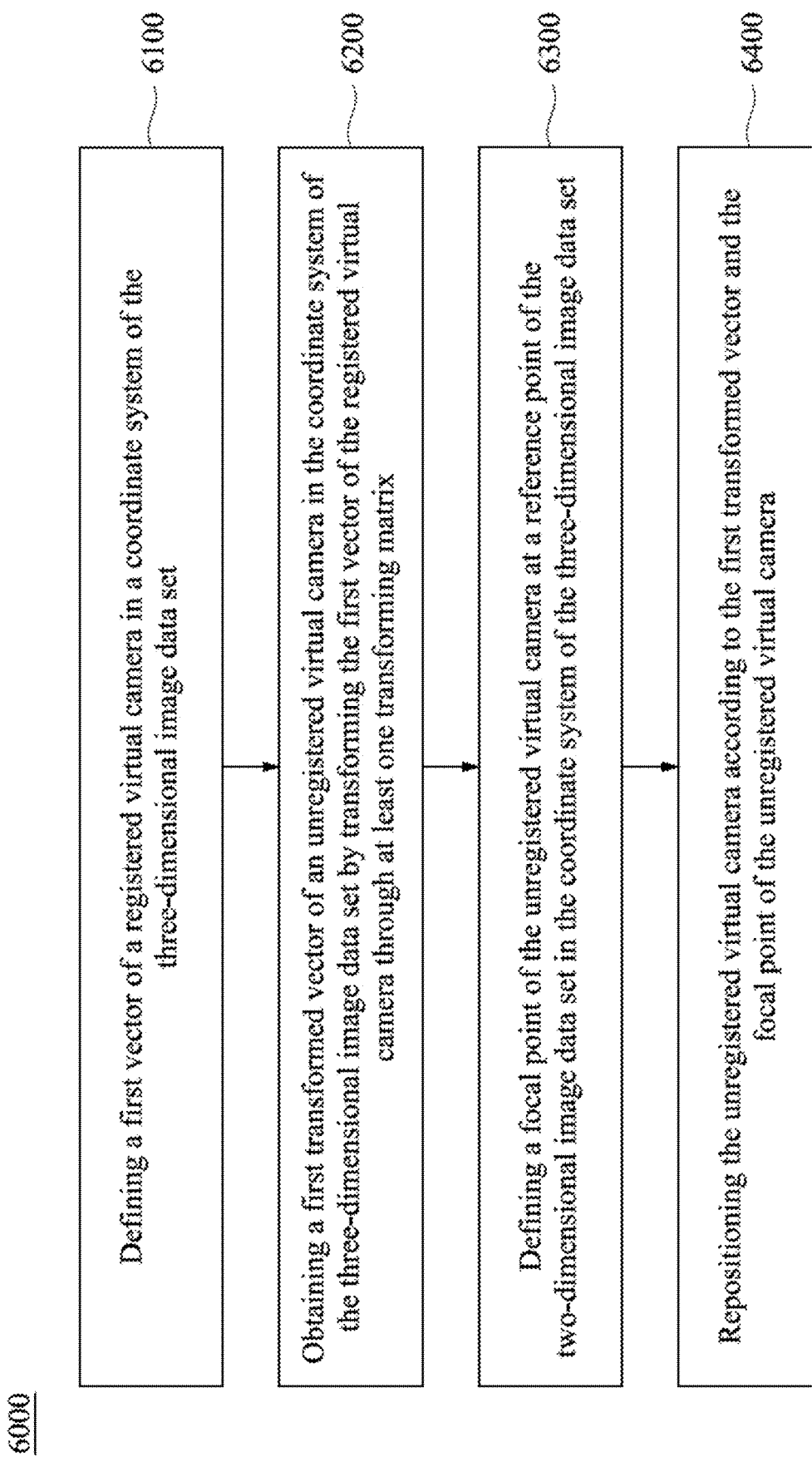
FIG. 13 depicts a flow diagram of a method for registering a two-dimensional image data set with a three-dimensional image data set of a body of interest according to one embodiment of the present disclosure.

The step 5600 for realignment in the method 5000 will be described in the following FIG. 13. FIG. 13 depicts a flow diagram of a method 6000 for realignment according to one embodiment of the present disclosure. In clinical practice, the two-dimensional image to three-dimensional registration procedure fails in the alignment stages from time to time. It may result from neither of AP nor LA two-dimensional images don't successfully align with the DRR images generated according to the three-dimensional image data set. However, the alignment failure is caused more often by only one of the two-dimensional images fails to align with the corresponding DRR image. Navigation system in prior art is programmed to stop proceed the registration procedure once any kind of failure abovementioned occurs. The consequence is to technicians or surgeons have to go back to the first step and redo it again. This significantly slows down the whole process of registration. In the present embodiment, the navigation system 1000 can address this issue by performing the realignment stage.

Referring to FIG. 2 and FIG. 13, if a LA DRR image, which is also known as LA three-dimensional reconstructed image, doesn't align with the LA C-arm X-ray image, which is also known as the two-dimensional image, and they need realignment, the processor 1120 may obtain a spatial parameter of a AP virtual camera corresponding to the AP DRR image which is successfully registered with the AP C-arm X-ray image in the previous steps. In view of the above, the AP virtual camera is regard as a registered virtual camera in the following description, and the LA virtual camera is regard as an unregistered virtual camera in the following description. However, the present disclosure is not limited to the above-mentioned embodiments, the AP virtual camera can be the unregistered virtual camera, and the LA virtual camera can be the registered virtual camera depending on actual situations.

Figure 14:
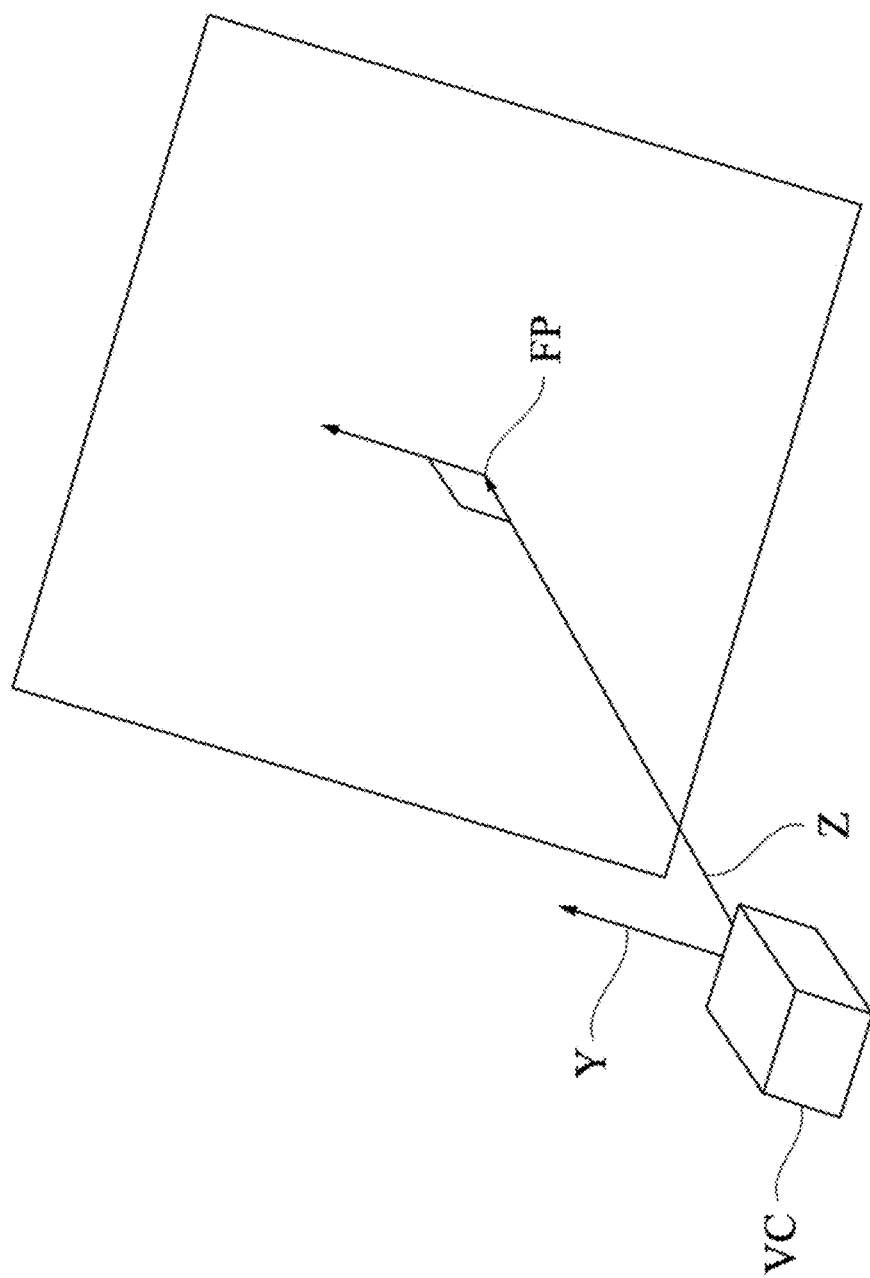
FIG. 14 depicts a schematic diagram of a virtual camera simulated by the calculating device of the navigation system shown in FIG. 1 according to one embodiment of the present disclosure.

For facilitating the understanding of the method 6000 in FIG. 1 reference is made to FIG. 14, which depicts a schematic diagram of a virtual camera VC according to one embodiment of the present disclosure. It is noted that the virtual camera VC in FIG. 14 is used to illustrate the concept of the present disclosure. The spatial parameter of the virtual camera VC may include kinds of position and/or orientation information such as but not limited to vectors. Both of the registered virtual camera and the unregistered virtual camera can be illustrated by FIG. 14, for example, each of the spatial parameter of the registered virtual camera and the unregistered virtual camera may include a vector of axis Z and an axis Y and also a focal point FP, respectively, defined in the coordination system of the three-dimensional subject generated by the three-dimensional image data set. Alternatively, the focal point FP may be accessed by the processor 1120 from the database 1200 separately instead of included in the spatial parameter. For identification purpose, the registered virtual camera will be labeled as VC1, and its axes and focal point will be labeled as Z1, Y1 and FP1 in the following description. Besides, the unregistered virtual camera will be labeled as VC2, and its axes and focal point will be labeled as Z2, Y2 and FP2 in the following description.

Referring to FIG. 2, FIG. 13, and FIG. 14, in operation, the step 6100 is performed by the processor 1120 to obtain a first vector from a spatial parameter of a registered virtual camera in the coordinate system of the three-dimensional image data set. For example, the processor 1120 may obtain the axis Z1 from the spatial parameter of the registered virtual camera VC1 in a coordinate system of the three-dimensional image data set pre-stored in the database 1200.

The step 6200 is performed by the processor 1120 to obtain a first transformed vector from a spatial parameter of an unregistered virtual camera in the coordinate system of the three-dimensional image data set by transforming the first vector of the registered virtual camera through at least one transforming matrix. For example, the processor 1120 may obtain the axis Z2 from the spatial parameter of the unregistered virtual camera VC2 in the coordinate system of the three-dimensional image data set by transforming the axis Z1 of the registered virtual camera VC1 through a programmed or pre-stored transforming matrix which is established by the processor 1120 according to the spatial relation of the particular components in the navigation system 1000.

The step 6300 is performed by the processor 1120 to obtain a focal point of the unregistered virtual camera at a reference point of the unregistered LA X-ray image, which is the unregistered two-dimensional image of the two-dimensional image data set, in the coordinate system of the three-dimensional image data set. For example, the processor 1120 may obtain a focal point FP2 of the unregistered virtual camera VC2 at a central point of calibrators of the two-dimensional image in the coordinate system of the three-dimensional image data set according to the previously performed unsuccessful registration.

The step 6400 is performed by the processor 1120 to reposition the unregistered virtual camera according to the first transformed vector and the focal point of the unregistered virtual camera for generating an update reconstructed image based on reposition of the unregistered virtual camera. For example, the unregistered virtual camera VC2 may be simulatively moved from its original position to the position calculated by the processor 1120 according to the axis Z2 of the unregistered virtual camera VC2 and the focal point FP2 of the unregistered virtual camera VC2.

In some embodiments, the first vector of the registered virtual camera is from the position of the registered virtual camera to the focal point of the registered virtual camera. For example, as shown in FIG. 14, the axis Z1 of the registered virtual camera VC1 is from the position of the registered virtual camera VC1 to the focal point FP1 of the registered virtual camera VC1.

In some embodiments, the first vector is defined as the Z axis (e.g., the axis Z1 in FIG. 14) of the registered virtual camera (e.g., the registered virtual camera VC1 in FIG. 14) in a coordinate system of the three-dimensional image data set.

In some embodiments, the processor 1120 is configured to obtain the plurality of commands from the memory 1110 to perform following steps: obtaining a second vector from a spatial parameter of the registered virtual camera in the coordinate system of the three-dimensional image data set; and obtaining a second transformed vector from a spatial parameter of the unregistered virtual camera in the coordinate system of the three-dimensional image data set according to the second vector of the registered virtual camera For example, the processor 1120 may obtain the axis Y1 from the spatial parameter of the registered virtual camera VC1 in a coordinate system of the three-dimensional image data set. The processor 1120 may obtain the axis Y2 three-dimensional of the unregistered virtual camera VC2 in the coordinate system of the three-dimensional image data set according to the axis Y1 from the spatial parameter of the registered virtual camera VC1.

In some embodiments, the second vector is from the central point (e.g., the point FP in FIG. 14) to the top edge (e.g., the top edge in FIG. 14) of a reconstructed image obtained by the registered virtual camera (e.g., the registered virtual camera VC1 in FIG. 14) parallel to the reconstructed image.

In some embodiments, the second vector is defined as the Y axis (e.g., the axis Y1 in FIG. 14) from the spatial parameter of the registered virtual camera (e.g., the registered virtual camera VC1 in FIG. 14) in a coordinate system of the three-dimensional image data set.

It is noted that, the present disclosure is not limited to the structures and the operations as shown in FIG. 13 and FIG. 14, and it is merely an example for illustrating one of the implements of the present disclosure, In some embodiments, the two-dimensional image data set comprises a first and second two-dimensional images, and the at least one transforming matrix similar or identical to the previously disclosed herein comprises a first matrix which functions to transform the coordinate system of the first two-dimensional image to the coordinate system of the second two-dimensional image. For example, the two-dimensional image data set includes an AP two-dimensional image and a LA two-dimensional image, and the transforming matrix includes a first matrix which functions to transform the coordinate system of the AP two-dimensional image to the coordinate system of the LA two-dimensional image.

In some embodiments, the reference point is at the central point of a calibrator module in the two-dimensional image data set in the coordinate system of the three-dimensional image data set. For example, the reference point is at the central point, which is also called the origin, of a calibrator module which is shown on the unregistered AP or LA X-ray two-dimensional image included in the two-dimensional image data set. The reference point is simulatively positioned and orientated in the coordinate system of the three-dimensional image data set for further function by the program of the navigation system 1000.

In some embodiments, the at least one transforming matrix comprises second matrix and a third matrix, wherein the second matrix which functions to transform the coordinate system of a reference mark to the coordinate system of the three-dimensional image data set and the third matrix which functions to transform the coordinate system of the reference mark to the coordinate system of a tracker module. For example, the at least one transforming matrix includes a second matrix and a third matrix. The second matrix which functions to transform the coordinate system of the calibrators 1510, 1530 and the dynamic reference frames 1520A in FIG. 1 to the coordinate system of the 3D image data set store in the database 1200 in FIG. 1. The third matrix which functions to transform the coordinate system of the calibrators 1510, 1530 and the dynamic reference frames 1520A in FIG. 1 to the coordinate system of the tracker 1400 in FIG. 1. The transforming matrix and the transformation of coordinate systems are well-known in the state of art. More, information can be found in L. Dorst, etc., Geometric Algebra For Computer Science, published by Morgan Kaufmann Publishers and M. N. Oosterom, etc., Navigation of a robot-integrated fluorescence laparoscope in preoperative SPECT/CT and intraoperative freehand SPECT imaging data: A phantom study, August 2016, Journal of Biomedical Optics 21(8):086008, which are incorporated herein by reference.

Figure 15:
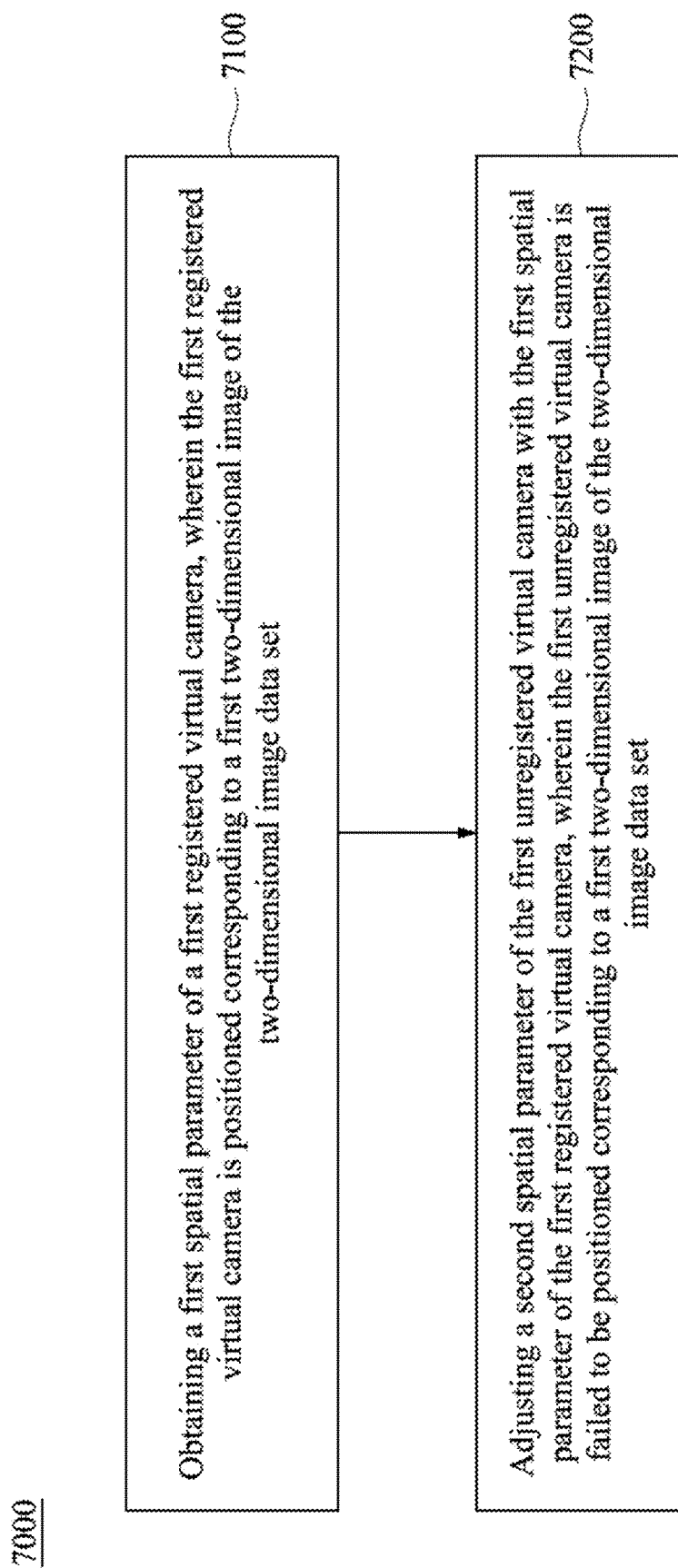
FIG. 15 depicts a flow diagram of a method for registering a two-dimensional image data set with a three-dimensional image data set of a body of interest according to one embodiment of the present disclosure.

The step 5600 for realignment in the method 5000 in FIG. 12 will be described in the following FIG. 15. FIG. 15 depicts a flow diagram of a method 7000 for realignment according to one embodiment of the present disclosure. Referring to FIG. 2 and FIG. 15, if an unregistered virtual camera corresponding to the vertebra V1 as shown in FIG. 5 or FIG. 7 needs realignment, the processor 1120 may find a registered virtual camera corresponding to the vertebra V0 or V2 as shown in FIG. 5 or FIG. 7.

Referring to FIG. 2 and FIG. 15, in operation, the step 7100 is performed by the processor 1120 to obtain a first spatial parameter of a first registered virtual camera, wherein the first registered virtual camera is positioned corresponding to a first two-dimensional image of the two-dimensional image data set. For example, the processor 1120 may obtain the first spatial parameter of the registered virtual camera corresponding to the vertebra V0 or V2 as shown in FIG. 5 or FIG. 7. The registered virtual camera is positioned corresponding to the two-dimensional image related to the vertebra V0 or V2 as shown in FIG. 4 or FIG. 6.

Referring to FIG. 2 and FIG. 15, in operation, the step 7200 is performed by the processor 1120 to adjust a second spatial parameter of the first unregistered virtual camera with the first spatial parameter of the first registered virtual camera for generating an update reconstructed image based on reposition of the first unregistered virtual camera, wherein the first unregistered virtual camera is failed to be positioned corresponding to the first two-dimensional image of the two-dimensional image data set. For example, the processor 1120 may adjust the second spatial parameter of the unregistered virtual camera corresponding to the vertebra V1 as shown in FIG. 6 or FIG. 7 with the first spatial parameter of the registered virtual camera corresponding to the vertebra V0 or V2 as shown in FIG. 5 or FIG. 7. The unregistered virtual camera is failed to be positioned corresponding to the two-dimensional image related to the vertebra V1 as shown in FIG. 4 or FIG. 6.

In some embodiments, a first part of the body of interest is included in the first two-dimensional image, a second part of the body of interest is included in the first two-dimensional image, and the first part and the second part of the body of interest are adjacent. For example, the object 9000 is a patient under vertebral disorder which needs an operation for stabilizing three vertebral levels. The three vertebral levels are together considered as the body of interest and shown in FIG. 4 and FIG. 6. According to the success or failure of the alignment with the three-dimensional image data set, the vertebral levels can be categorized into two parts.

The first part includes the vertebra V0 or V2, and the second part includes the vertebra V1. In more detail, the first part of the body of interest in FIG. 1 is included in the first two-dimensional images corresponding to the vertebra V0 or V2. The first two-dimensional images are FIG. 4 as the AP X-ray image and FIG. 6 as the LA X-ray image. The second part of the body of interest in FIG. 1 is included in the first two-dimensional images corresponding to the vertebra V1. The first two-dimensional images are FIG. 4 and FIG. 6. As can be seen in FIG. 4 and FIG. 6, the vertebra V0 or V2 included in the first part of the object 9000 is adjacent to the vertebra V1 included in the second part of the object 9000 corresponding to the vertebra V1.

In some embodiments, the first part of the body of interest is defined according to a first marker in the first two-dimensional image of the two-dimensional image data set, and the second part of the body of interest is defined according to a second marker in the first two-dimensional image of the two-dimensional image data set. For example, the first part of the body of interest of the object 9000 in FIG. 1 is defined by the program of the navigation system 1000 to automatically recognize the image boundary of the vertebra which is mark as V0 or V2 on the two-dimensional images in FIG. 4 and FIG. 6. The second part of the body of interest of the object 9000 in FIG. 1 is defined by the program of the navigation system 1000 to automatically recognize the image boundary of the vertebra which is mark as V1 on the two-dimensional image in FIG. 4 and FIG. 6 by the same measure as the first part.

In some embodiments, the first spatial parameter of the first registered virtual camera comprises a position and/or an orientation data which are used to define a position and/or an orientation of the first registered virtual camera corresponding to the three-dimensional subject or the three-dimensional subject corresponding to the first registered virtual camera. For example, the first spatial parameter of the registered virtual camera corresponding to the vertebra V0 or V2 as shown in FIG. 5 or FIG. 7 includes a position and/or an orientation data which are used to define a position and/or an orientation of the registered virtual camera corresponding to the three-dimensional object generated from the three-dimensional image data set or the three-dimensional object corresponding to the registered virtual camera.

In some embodiments, the second spatial parameter of the first unregistered virtual camera comprises a position and/or an orientation data which are used to define a position and/or an orientation of the first unregistered virtual camera corresponding to the three-dimensional subject or the three-dimensional subject corresponding to the first registered virtual camera. For example, the second spatial parameter of the unregistered virtual camera corresponding to the vertebra V1 as shown in FIG. 5 or FIG. 7 includes a position and/or an orientation data which are used to define a position and/or an orientation of the unregistered virtual camera corresponding to the three-dimensional object generated from the three-dimensional image data set or the three-dimensional object corresponding to the registered virtual camera.

In some embodiments, the first registered virtual camera is positioned according to comparison of the similarity values calculated according to different reconstructed images obtained from the three-dimensional image data set and the first two-dimensional image of the two-dimensional image data. For example, the registered virtual camera is positioned according to comparison of the similarity values calculated according to different DRR images obtained from the three-dimensional image data set and the two-dimensional image related to the vertebra V0 or V2 as shown in FIG. 4 or FIG. 6.

In some embodiments, each of the similarity values is calculated by local normalized correlation (LNC), sum of squared differences (SSD), normalized cross-correlation (NCC), or correlation ratio (CR).

In some embodiments, the processor 1120 is further used to perform the following steps: defining the second spatial parameter of the first unregistered virtual camera to be a N spatial parameter; determining whether a N-M spatial parameter of the first registered virtual camera is positioned corresponding to the first two-dimensional image of the two-dimensional image data set, wherein N and M are integers, and M is less than N, and if the N-M spatial parameter of the first registered virtual camera is positioned corresponding to the first two-dimensional image of the two-dimensional image data set, defining the N-M spatial parameter to be the first spatial parameter of the first registered virtual camera.

For example, the processor 1120 of the calculating device 1100 may define the second spatial parameter of the unregistered virtual camera to be a N spatial parameter. The processor 1120 of the calculating device 1100 may determine whether a N-M spatial parameter of the registered virtual camera is positioned corresponding to the two-dimensional image related to the vertebra V0 or V2 as shown in FIG. 4 or FIG. 6, wherein N and M are integers, and M is less than N. The processor 1120 of the calculating device 1100 may define the N-M spatial parameter to be the first spatial parameter of the registered virtual camera if the N-M spatial parameter of the registered virtual camera is positioned corresponding to the two-dimensional image related to the vertebra V0 or V2 as shown in FIG. 4 or FIG. 6. Specifically, the N spatial parameter is corresponding to the unregistered virtual camera. The navigation system 1000 may find the N-M spatial parameter which is corresponding to the registered virtual camera, and the N-M spatial parameter will be used in the unregistered virtual camera for facilitating the process.

In some embodiments, the processor 1120 is further used to perform the following steps: defining the second spatial parameter of the first unregistered virtual camera to be a N spatial parameter; determining whether a N+M spatial parameter of the first registered virtual camera is positioned corresponding to the first two-dimensional image of the two-dimensional image data set, wherein N and M are integers, and M is less than N; and if the N+M spatial parameter of the first registered virtual camera is positioned corresponding to the first two-dimensional image of the two-dimensional image data set, defining the N+M spatial parameter to be the first spatial parameter of the first registered virtual camera.

For example, the processor 1120 of the calculating device 1100 may defining the second spatial parameter of the unregistered virtual camera to be a N spatial parameter. The processor 1120 of the calculating device 1100 may determine whether a N+M spatial parameter of the registered virtual camera is positioned corresponding to the two-dimensional image related to the vertebra V0 or V2 as shown in FIG. 4 or FIG. 6, wherein N and M are integers, and M is less than N. The processor 1120 of the calculating device 1100 may define the N+M spatial parameter to be the first spatial parameter of the registered virtual camera if the N+M spatial parameter of the first registered virtual camera is positioned corresponding to the two-dimensional image related to the vertebra V0 or V2 as shown in FIG. 4 or FIG. 6.

It is noted that, the present disclosure is not limited to the operations as shown in FIG. 15, and it is merely an example for illustrating one of the implements of the present disclosure.

As discussed above, the step 5600 for realignment in the method 5000 in FIG. 12 includes but not limited to two realignment processes in FIG. 13 and FIG. 15. For facilitating the understanding regarding the realignment processes in FIG. 13 and FIG. 15, reference is made to FIG. 16, which depicts a schematic diagram of a flow diagram of a method 8000 for realignment according to one embodiment of the present disclosure.

Figure 16:
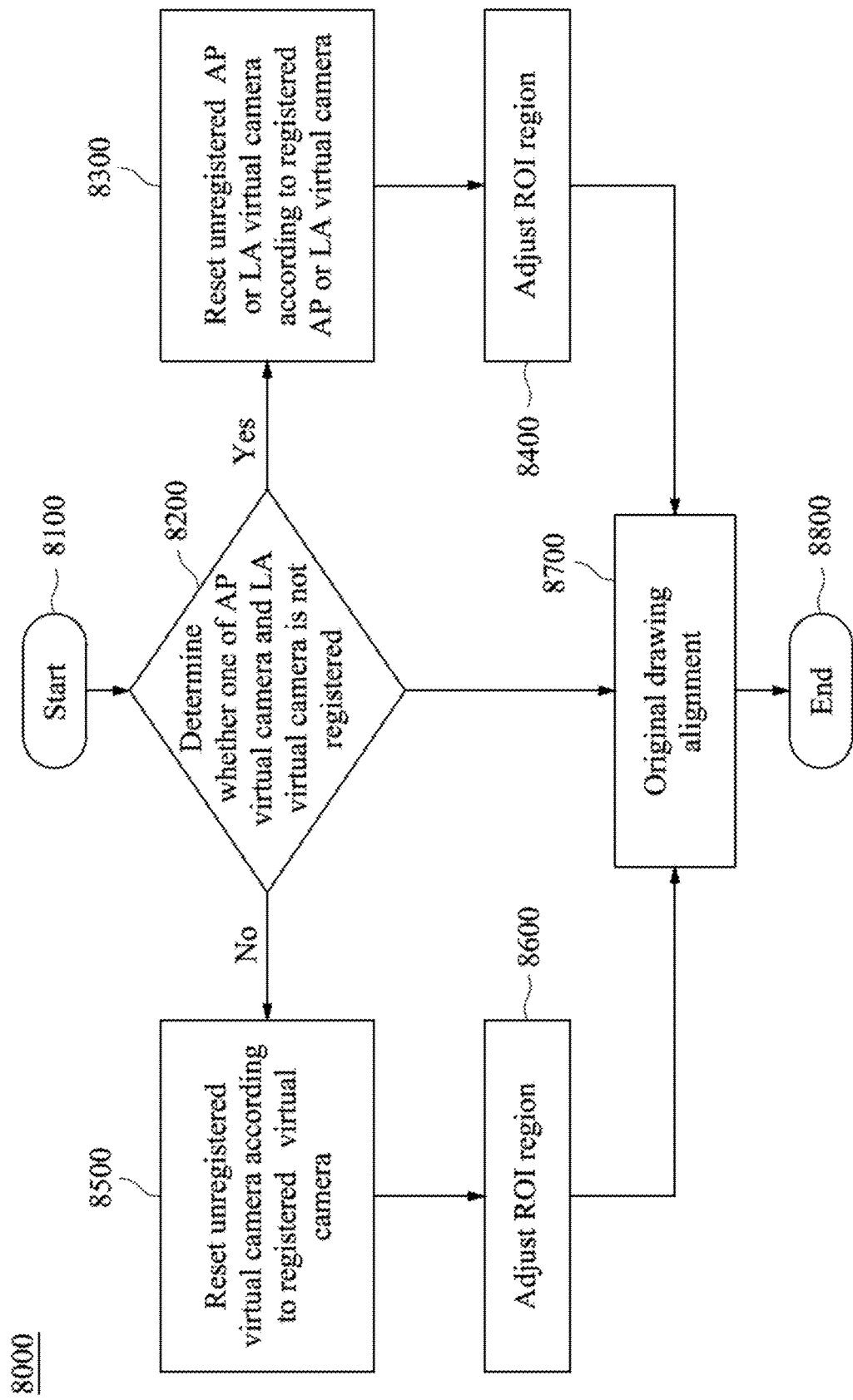
FIG. 16 depicts a flow diagram of a method for registering a two-dimensional image data set with a three-dimensional image data set of body of interest according to one embodiment of the present disclosure.

Reference is now made to both FIG. 2 and FIG. 16. In operation, the step 8200 is performed by the processor 1120 to determine whether one of the AP DRR image acquired by the AP virtual camera and the LA DRR image acquired by the LA virtual camera is not registered. If it is determined that one of the DRRs acquired by the AP virtual camera or the LA virtual camera is not registered, the method 8000 proceeds to step 8300. Specifically, if the AP virtual camera is not registered, the step 8300 is performed by the processor 1120 to reset the AP virtual camera which is not registered according to the LA virtual camera which is registered. The method 6000 in FIG. 13 is similar to the step 8300 in method 8000. When the DRR image acquired by the AP virtual camera or the LA virtual camera is not registered, the method 6000 will find out and use a registered virtual camera to reset the unregistered virtual camera. Subsequently, the step 8700 is performed by the processor 1120 to execute the original drawing alignment by using the reset virtual camera. In addition, the step 8400 is performed by the processor 1120 to adjust the ROI region for avoiding the interference, After the step 8200 is performed, if it is determined that none of the DRR images acquired by the AP virtual c era and the LA virtual camera is registered, the method 8000 proceeds to step 8500. Specifically, if the AP virtual camera and the LA virtual camera are not registered, it means the AP and LA DRR images corresponding to a first vertebra are all failed to be registered. The step 8500 is performed by the processor 1120 to find out another AP virtual camera and another LA virtual camera corresponding to a second vertebra, wherein the DRRs of the virtual cameras are successfully registered with the three-dimensional image data set. Thereafter, the processor 1120 may reset the unregistered AP virtual camera and the unregistered LA virtual camera corresponding to the first vertebra according to the spatial parameter or data of the registered AP virtual camera and the registered LA virtual camera corresponding to the second vertebra. The method 7000 in FIG. 15 is similar to the step 8500 in method 8000. When the DRR images acquired by the AP virtual camera and the LA virtual camera corresponding to the first vertebra are all failed to be registered, the method 7000 will find out and use the spatial parameter or data of the registered AP virtual camera and the registered LA virtual camera corresponding to the second vertebra to reset the unregistered AP virtual camera and the unregistered LA virtual camera corresponding to the first vertebra. Subsequently, the step 8700 is performed by the processor 1120 to execute the original drawing alignment by using the reset virtual camera. In addition, the step 8600 is performed by the processor 1120 to adjust the ROI region for avoiding the interference It can be understood from the embodiments of the present disclosure that application of the present disclosure has the following advantages. The method and the navigation system for registering a two-dimensional image data set with a three-dimensional image data set of a body of interest of the present disclosure can pre-store three-dimensional image data set of the body of interest in the database, and then take merely two X-ray images (two-dimensional images) of the patient (the body of interest) during the surgery so as to establish the relation between the two-dimensional image data set and the three-dimensional image data set. Thereafter, the method and the navigation system of the present disclosure may provide an accurate navigation during the surgery by using the pre-store three-dimensional image data set. Since the method and the navigation system of the present disclosure merely take two X-ray images (two-dimensional images) of the body of interest, the radiation exposure to the patient (the body of interest) is reduced by over 98%. In view of the above, the present disclosure may provide the method and the navigation system for executing the two-dimensional to three-dimensional registration in a more accurate and efficient way.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for registering a two-dimensional image data set with a three-dimensional image data set of a body of interest, the method comprising:

adjusting a first virtual camera according to a distance parameter calculated corresponding to the two-dimensional image data set and the body of interest;

rotating the first virtual camera according to an angle difference between a first vector and a second vector, wherein the first vector is calculated from two spatial marks in the three-dimensional image data set, and the second vector is calculated from two first plain marks in the two-dimensional image data set; and rotating the first virtual camera according to an angle which is corresponding to a maximum similarity value of a plurality of similarity values calculated in accordance with reconstructed images of the three-dimensional image data set, wherein the reconstructed images include one reconstructed image generated by the first virtual camera and other reconstructed images generated by other virtual cameras, wherein the one reconstructed image and the other reconstructed images have different angles or different pixels, and wherein the two-dimensional image data set and the three-dimensional image data set are pre-processed for registration in a navigation system after rotating the first virtual camera according to the angle which is corresponding to the maximum similarity value.

2. The method of claim 1, wherein the distance parameter is calculated according to the two first plain marks in the two-dimensional image data set, and the method comprising:

adjusting the reconstructed images generated by the first virtual camera according to the distance parameter.

3. The method of claim 1, wherein the distance parameter is calculated according to a distance between an estimated position of an emitter and an estimated position of the body of interest.

4. The method of claim 3, wherein the estimated position of the emitter is calculated according to the two-dimensional image data set, and the estimated position of the body of interest is at a position at which a first virtual line and a second virtual line are the closest.

5. The method of claim 4, wherein the two-dimensional image data set includes first and second two-dimensional images, the first virtual line is generated between the estimated position of the emitter and a central point of at least two reflectors which are radiated when a first two-dimensional image data set is captured, the second virtual line is generated between the estimated position of the emitter and the central point of the at least two reflectors which are radiated when a second two-dimensional image data set is captured.

6. The method of claim 1, wherein the two-dimensional image data set includes a first two-dimensional image, the first vector is calculated from the two spatial marks in the three-dimensional image data set generated by the first virtual camera, and the second vector is calculated by the two first plain marks in a first two-dimensional image data.

7. The method of claim 6, wherein the two-dimensional image data set includes a second two-dimensional image, the second vector is calculated from two second plain marks in a second two-dimensional image data.

8. The method of claim 1, wherein an adjusted first virtual camera is generated after the rotation of the first virtual camera, and the method comprise:

rotating the adjusted first virtual camera according to the angle which is corresponding to an adjusted maximum similarity value of the plurality of similarity values calculated in accordance with adjusted reconstructed images, wherein the adjusted reconstructed images include one adjusted reconstructed image generated by the adjusted first virtual camera and other adjusted reconstructed images generated by other virtual cameras, wherein the one adjusted reconstructed image and the other adjusted reconstructed images have different angles.

9. The method of claim 1, wherein an adjusted maximum similarity value of the plurality of similarity values is calculated in accordance with adjusted reconstructed images, wherein the adjusted reconstructed images include one adjusted reconstructed image generated by an adjusted first virtual camera and other adjusted reconstructed images generated by other virtual cameras, wherein the one adjusted reconstructed image and the other adjusted reconstructed images have different angles or different pixels.

10. The method of claim 1, further comprising:
adjusting the first virtual camera of a plurality of virtual cameras corresponding to the three-dimensional image data set according to a matrix corresponding to the two-dimensional image data set.

11. A navigation system for registering a two-dimensional image data set with a three-dimensional image data set of a body of interest, comprising:
a memory, configured to store a plurality of commands; and
a processor, configured to obtain the plurality of commands from the memory to perform following steps:
adjusting a first virtual camera according to a distance parameter calculated corresponding to the two-dimensional image data set and the body of interest;
rotating the first virtual camera according to an angle difference between a first vector and a second vector, wherein the first vector is calculated from two spatial marks in the three-dimensional image data set, and the second vector is calculated from two first plain marks in the two-dimensional image data set; and
rotating the first virtual camera according to an angle which is corresponding to a maximum similarity value of a plurality of similarity values calculated in accordance with reconstructed images of the three-dimensional image data set,
wherein the reconstructed images include one reconstructed image generated by the first virtual camera and other reconstructed images generated by other virtual cameras,
wherein the one reconstructed image and the other reconstructed images have different angles or different pixels, and
wherein the two-dimensional image data set and the three-dimensional image data set are pre-processed for registration in a navigation system after rotating the first virtual camera according to the angle which is corresponding to the maximum similarity value.

12. The navigation system of claim 11, wherein the distance parameter is calculated according to the two first plain marks in the two-dimensional image data set, and the processor is further configured to perform following step:
adjusting the reconstructed images generated by the first virtual camera according to the distance parameter.

13. The navigation system of claim 11, wherein the distance parameter is calculated according to a distance between an estimated position of an emitter and an estimated position of the body of interest.

14. The navigation system of claim 13, wherein the estimated position of the emitter is calculated according to the two-dimensional image data set, and the estimated position of the body of interest is at a position at which a first virtual line and a second virtual line are the closest.

15. The navigation system of claim 14, wherein the two-dimensional image data set includes first and second two-dimensional images, the first virtual line is generated between the estimated position of the emitter and a central point of at least two reflectors which are radiated when a first two-dimensional image data set is captured, the second virtual line is generated between the estimated position of the emitter and the central point of the at least two reflectors which are radiated when a second two-dimensional image data set is captured.

16. The navigation system of claim 11, wherein the two-dimensional image data set includes a first two-dimensional image, the first vector is calculated from the two spatial marks in the three-dimensional image data set generated by the first virtual camera, and the second vector is calculated by the two first plain marks in a first two-dimensional image data.

17. The navigation system of claim 16, wherein the two-dimensional image data set includes a second two-dimensional image, the second vector is calculated from two second plain marks in a second two-dimensional image data.

18. The navigation system of claim 11, wherein an adjusted first virtual camera is generated after the rotation of the first virtual camera, and the processor is further configured to perform following step:
rotating the adjusted first virtual camera according to the angle which is corresponding to an adjusted maximum similarity value of the plurality of similarity values calculated in accordance with adjusted reconstructed images, wherein the adjusted reconstructed images include one adjusted reconstructed image generated by the adjusted first virtual camera and other adjusted reconstructed images generated by other virtual cameras, wherein the one adjusted reconstructed image and the other adjusted reconstructed images have different angles.

19. The navigation system of claim 11, wherein an adjusted maximum similarity value of the plurality of similarity values is calculated in accordance with adjusted reconstructed images, wherein the adjusted reconstructed images include one adjusted reconstructed image generated by an adjusted first virtual camera and other adjusted reconstructed images generated by other virtual cameras, wherein the one adjusted reconstructed image and the other adjusted reconstructed images have different angles or different pixels.

20. The navigation system of claim 11, wherein the processor is further configured to perform following step:
adjusting the first virtual camera of a plurality of virtual cameras corresponding to the three-dimensional image data set according to a matrix corresponding to the two-dimensional image data set.

* * * * *